(12) United States Patent
Grund et al.

(10) Patent No.: US 8,536,370 B2
(45) Date of Patent: Sep. 17, 2013

(54) LOW CHLORINE, MULTI-STAGED METHOD FOR PRODUCING CYCLOALIPHATIC DISOCYANATES

(75) Inventors: Gerda Grund, Coesfeld (DE); Manfred Kreczinski, Herne (DE); Stephan Kohlstruk, Duelmen (DE); Christian Lettmann, Coesfeld (DE)

(73) Assignee: Evonik Degussa GmbH, Essen (DE)

( * ) Notice: Subject to any disclaimer, the term of this patent is extended or adjusted under 35 U.S.C. 154(b) by 342 days.

(21) Appl. No.: 12/922,280

(22) PCT Filed: May 18, 2009

(86) PCT No.: PCT/EP2009/055986
§ 371 (c)(1),
(2), (4) Date: Sep. 13, 2010

(87) PCT Pub. No.: WO2009/144148
PCT Pub. Date: Dec. 3, 2009

(65) Prior Publication Data
US 2011/0028755 A1    Feb. 3, 2011

(30) Foreign Application Priority Data
May 27, 2008  (DE) .......................... 10 2008 002 002

(51) Int. Cl.
*C07C 263/12*   (2006.01)
*C07C 263/06*   (2006.01)

(52) U.S. Cl.
USPC ........................................... 560/338; 560/344

(58) Field of Classification Search
USPC ........................................... 560/338
See application file for complete search history.

(56) References Cited

U.S. PATENT DOCUMENTS

| 4,554,378 A * | 11/1985 | Nafziger et al. ............. 564/332 |
| 7,307,186 B2 * | 12/2007 | Kohlstruk et al. ............. 560/330 |
| 2005/0043561 A1 * | 2/2005 | Kohlstruk et al. ............. 560/345 |

FOREIGN PATENT DOCUMENTS

| EP | 0 000 778 | 2/1979 |
| EP | 0 043 933 | 1/1982 |
| EP | 1 512 681 | 3/2005 |

* cited by examiner

Primary Examiner — Johann R Richter
Assistant Examiner — Kofi Adzamli
(74) Attorney, Agent, or Firm — Oblon, Spivak, McClelland, Maier & Neustadt, L.L.P.

(57) ABSTRACT

Low chlorine, multi-staged method for producing cycloaliphatic diisocyanates. The invention relates to a multi-staged method for the continuous low-chlorine production of cycloaliphatic diisocyanates, comprising the synthesis of diaminodipheynl alkanes, the hydration thereof into the corresponding cycloaliphatic diamines and the subsequent conversion of cycloaliphatic diamines to the corresponding cycloalkylene biscarbamates and the thermal cleaving of the latter into the cycloaliphatic diisocyanates and alcohol.

45 Claims, No Drawings

LOW CHLORINE, MULTI-STAGED METHOD FOR PRODUCING CYCLOALIPHATIC DISOCYANATES

CROSS-REFERENCE TO RELATED APPLICATIONS

This application is a National Stage of PCT/EP2009/055986 filed on May 18, 2009. This application is based upon and claims the benefit of priority to German Application No. 10 2008 002 002.8 filed on May 27, 2008.

BACKGROUND OF THE INVENTION

The invention relates to a low-chlorine multistage process for continuous chlorine-free preparation of cycloaliphatic diisocyanates, which comprises the synthesis of diaminodiphenylalkanes, the hydrogenation thereof to the corresponding cycloaliphatic diamines and the subsequent conversion of cycloaliphatic diamines to the corresponding cycloalkylenebiscarbamates, and the thermal cleavage of the latter to the cycloaliphatic diisocyanates and alcohol.

It is known that diaminodiphenylalkanes (which also include substituted diphenyls and systems with fused aromatic rings (bicyclic or tricyclic ring systems)) can be prepared by condensation of an aromatic amine, for example aniline and aldehyde, over acidic catalysts. In the context of this invention, diaminodiphenylalkanes are also referred to as aromatic diamines.

The reaction is effected in such a way that N-alkyl compounds are first formed from an aromatic amine (aniline) and aldehyde. These precondensates then react further in the presence of acidic catalysts to give animals. These animals are subsequently rearranged under the action of an acidic catalyst to give diaminodiphenylalkanes.

In the prior art, the preparation of diaminodiphenylalkanes from the condensation of aromatic amines and aldehyde, especially aniline and formaldehyde, is frequently carried out. According to the reaction variant, either the condensation product of aniline and formaldehyde is first prepared and then rearranged in the presence of acids, for example hydrochloric acid, or else the condensation has already been carried out in the presence of acids under rearrangement conditions.

One disadvantage of this method is that salt-containing wastewaters are obtained in the homogeneous catalysis with mineral acids, especially with hydrochloric acid, and arise in neutralization of the acids. The chlorine salts are considered to be particularly critical. Furthermore, the aqueous mineral acids lead to corrosion problems in the production plants. Processes have therefore been developed in the further prior art in which appropriate heterogeneous catalysts are used. In addition to acidic ion exchangers, it is also possible to use acidic synthetic or natural silicas or aluminas, such as zeolites or clay minerals.

In U.S. Pat. No. 4,294,981, in such a process, the condensation is performed in the presence of a strong aqueous acid, after which the acid is removed by solvent extraction. The rearrangement is again carried out in the presence of strong acid which is used in a smaller amount. Diatomaceous earth, clays or zeolites can be used as the catalyst in this reaction stage.

DE-A-12 30 033 describes a process for preparing diaminodiphenylalkanes. This process uses silicon-containing clay, a synthetic silicon dioxide-aluminium oxide catalyst or a magnesium oxide-aluminium oxide catalyst.

A further reaction process for preparing diaminodiphenylalkanes is described in DE-A-14 93 431. This uses silicon dioxide, silicon dioxide-aluminium oxide or acid-treated aluminium oxide as a catalyst. Preference is given to silica gel or bentonite-type clay which contains silicon dioxide and aluminium oxide and is preferably acid-activated.

U.S. Pat. No. 4,071,558 describes a preparation process for preparing diaminodiphenylalkanes, in which an acid-activated clay catalyst, a silicon dioxide-aluminium oxide-containing cracking catalyst or a silicon dioxide-magnesium oxide catalyst is used.

U.S. Pat. No. 4,039,580 describes a preparation process in which the condensation of aniline and formaldehyde is performed in the absence of a catalyst and the condensation product is then reacted further in the presence of diatomaceous earth, clays or zeolites to give the diaminodiphenylmethane. Similar reactions are also described in U.S. Pat. No. 4,039,581.

The catalysts from the group of magnesium oxides or aluminium oxides, clay catalysts or silicon dioxide catalysts have not become established owing to their high costs, the low activities, the inhomogeneous quality and inadequate catalyst lifetimes.

The prior art therefore proposes, as a catalyst for preparing diaminodiphenylalkanes, an ion exchanger which possesses acidic groups. For instance, EP 0 043 933 A1 describes a process for preparing polyamine mixtures with a high proportion of 4,4'-diaminodiphenylmethane and a low proportion of 2,4'-diaminodiphenylmethane, in which the catalyst used is an ion exchanger based on a divinylbenzene/styrene copolymer. This ion exchanger possesses sulphonic acid groups, a specific surface area of 2 to 40 $m^2/g$ and a pore width of 0.5 to 40 nm. This wide range is demonstrated in the examples only by examples with pore widths of 1 nm. The acidic groups used for the catalyst are sulphonic acid groups. The yields in this process are in the range of 60 to 78%. Using the sulphonated styrene-divinylbenzene copolymer catalyst, it is possible to prepare diaminodiphenylmethanes which possess a high content of 4,4'-diaminodiphenylmethane. This isomer is especially required for further processing, specifically for conversion to corresponding diisocyanates of the diphenylmethane series, which constitute the starting materials in the preparation of polyurethanes or are used as coating raw materials. The publication further states that the proportion of 2,2'- and 2,4'-diisocyanatodiphenylmethane compounds has to be at a minimum because these isomers are undesired for many fields of application in the polyisocyanate sector. According to the prior art of EP 0 043 933, the resulting diaminodiphenylmethane compounds are subjected immediately to a phosgenation in order to prepare corresponding diisocyanates.

The process for preparing diaminodiphenylalkanes described in EP 0 043 933 has the disadvantage that it possesses low yields and, in spite of a high reaction temperature, very long reaction times are needed in order to achieve an industrially acceptable yield. A further disadvantage is that only a small proportion of 2,4'-isomer forms in the prior art process.

In addition to aromatic isocyanates, the corresponding aliphatic isocyanates are of particular significance in some specific fields.

The next stage in the preparation process of aliphatic isocyanates is the hydrogenation of the aromatic ring of the diaminodiphenylalkanes.

The hydrogenation of diaminodiphenylmethane (MDA) forms, from the 4,4'-isomer, 4,4'-trans/trans-, -cis/cis- and -cis/trans-diaminodicyclohexylmethane (PACM). The content of trans/trans-4,4'-diaminodicyclohexylmethane has a considerable influence on the crystallization tendency of the diisocyanate. When the trans/trans-4,4' fraction of the product is too high in the diisocyanate prepared from PACM by phosgenation or other processes, the diisocyanatodicyclohexylmethane may form crystals even at room temperature, which is a hindrance for the further processing to polyurethanes. Before the further processing, complicated process steps therefore have to be undertaken in order to reduce the content of 4,4'-isomer to an acceptable value, such that crystal formation no longer occurs. This is typically done by enriching the 2,4'-isomer.

A further requirement on the isomer content in the preparation of diaminodiphenylmethane is that a very low proportion of 2,2'-isomer must be present, since this isomer causes chain termination in the polymerization reaction in the later process step to polyurethanes.

In order to avoid this additional complexity, it is important for this reaction route that a particular isomer ratio is achieved as early as in the preparation of diaminodiphenylmethane.

According to the prior art to date, this isomer ratio is obtained by purifying and distilling the diaminodiphenylmethane in a complicated manner in order to be able to provide the isomers in the ratio needed for the further processing.

It is known that cycloaliphatic amines having one or more amino groups can be prepared by catalytic hydrogenation of the corresponding mono- or polycyclic aromatic amines having one or more amino groups and optionally further substituents.

For the hydrogenation, catalysts based on ruthenium (EP 1 366 812, DE 15 93 293, DE 19 48 566, EP 0 001 425), rhodium (EP 0 630 882, EP 66 212) or mixtures thereof (U.S. Pat. No. 5,545,756, EP 0 231 788) are frequently used.

In the hydrogenation of diaminodiphenylmethane, referred to hereinafter simply as MDA, to methylenedicyclohexyldiamine, referred to hereinafter simply as $H_{12}$MDA, especially formamide (EP 1 604 972) and MDA polymers (EP 1 149 629, EP 0 335 336) lead to a deactivation of the catalysts. When chloride is present in the MDA, it is absorbed by the catalyst and leads subsequently to increased formation of undesired polycyclic compounds (EP 0 324 190). The chloride has to be removed at regular intervals by washing the catalyst with water. This washing operation with water leads firstly to production shutdowns. Secondly, the reaction system subsequently has to be very substantially freed of water in order to minimize the formation of undesired hydroxyl compounds.

The synthetic access to isocyanates may be via a number of different routes. The oldest variant for industrial scale preparation of isocyanates, which is still prevalent to date, is the so-called phosgene route. The basis of this process is the reaction of amines with phosgene. The disadvantage of the phosgene process is the use of phosgene which, owing to its toxicity, its corrosivity and the high chlorine content, places particularly high demands on its handling on the industrial scale.

Process technology approaches which allow the use of phosgene for preparation of isocyanates to be avoided in industrial orders of magnitude are known. The term "phosgene-free process" is utilized in connection with the conversion of amines to isocyanates using alternative carbonylating agents, for example urea or dialkyl carbonate (EP 0 018 586, EP 0 355 443, U.S. Pat. No. 4,268,683, EP 0 990 644).

The basis of the so-called urea route is the urea-mediated conversion of diamines to diisocyanates via a two-stage process. In the first step, a diamine is reacted with alcohol in the presence of urea or urea equivalents (e.g. alkyl carbonates, alkyl carbamates) to give a diurethane, which typically passes through an intermediate purification stage and is then cleaved thermally in the second step to diisocyanate and alcohol (EP 0 355 443, U.S. Pat. Nos. 4,713,476, 5,386,053). Alternatively, the actual urethane formation may also be preceded by the separate preparation of a diurea by controlled reaction of the diamine with urea (EP 0 568 782). Also conceivable is a two-stage sequence consisting of partial reaction of urea with alcohol in the first step and subsequent metered addition and urethanization of the diamine in the second step (EP 0 657 420).

The thermal cleavage of urethanes to the corresponding isocyanates and alcohols has been known for some time and can be performed either in the gas phase at high temperatures or at relatively low temperatures in the liquid phase. However, a problem in both procedures is that, as a result of the thermal stress, undesired side reactions always also occur, which firstly reduce the yield and secondly lead to the formation of resinifying by-products which considerably disrupt the course of an industrial process as a result of depositions and blockages in reactors and workup apparatus.

There has therefore been no lack of attempts to achieve yield improvements by chemical and process technology measures, and to limit undesired by-product formation. For instance, a series of documents describes the use of catalysts which accelerate the cleavage reaction of the urethanes (DE 10 22 222, U.S. Pat. No. 3,919,279, DE 26 35 490). In fact, it is entirely possible in the presence of suitable catalysts—which are a multitude of basic, acidic and organometallic compounds—to increase the isocyanate yield compared to the uncatalysed variant. However, the formation of undesired by-products cannot be avoided even by virtue of the presence of a catalyst. The same applies to the additional use of inert solvents, as likewise recommended in U.S. Pat. No. 3,919, 279 and DE 26 35 490, in order to ensure homogeneous distribution of the heat supplied and of the catalyst in the reaction medium. In principle, the use of solvents which boil under reflux, however, has the consequence of a reduction in the space-time yield of isocyanates and is additionally afflicted with the disadvantage of an additional high energy demand.

The examples of thermally catalysed cleavage of monourethanes adduced in EP 0 054 817 describe the partial discharge of the reaction mixture to remove the resinifying by-products which form in the course of urethane cleavage. This procedure serves to prevent depositions and blockages in reactors and workup equipment. There are no indications to a yield-enhancing utilization of the partial discharge. EP 0 061 013 describes a similar approach to a solution, wherein the thermolysis in this case is performed in the presence of solvents whose task apparently consists in a better absorption of the nonvolatile by-products. Here too, the partial discharge is not utilized for the purpose of optimizing the yield.

EP 0 355 443 discloses that an increase in the yield can be achieved when the relatively high molecular weight, utilizable and unutilizable by-products formed during the cleavage of diurethanes in the cleavage reactor, to ensure a disruption-free and selective reaction, are discharged very substantially continuously from the reactor and then converted for the most part in the presence of alcohol, and then recycled into the diurethane preparation. The procedure described is associated with a high energy demand, since unutilizable by-products are removed by distillation from the effluent of the diurethane preparation, for which the entire diurethane has to be evaporated. In contrast to EP 0 355 443, the urethanization effluent, in the process of EP 0 566 925, is divided into two substreams of which only one is freed by distillation from its high-boiling, unutilizable by-products, before the combined diurethane streams are fed to the deblocking reaction in the cleavage reactor. In addition, the continuous cleavage reactor discharge in EP 0 566 925 is recycled directly, i.e. without a reurethanization step, into the diurethane synthesis.

The procedure of EP 0 566 925 has the consequence that a portion of the high boiler components from the diurethane synthesis passes via the deblocking stage back into the diurethane preparation and further into the diurethane purification procedure.

Possible processes which do not have the disadvantages of the prior art detailed, also guarantee good plant availability and a good process yield over the long term and additionally allow the saving of investment and energy costs are described in EP 1 512 680, EP 1 512 681, EP 1 512 682, EP 1 593 669, EP 1 602 643, EP 1 634 868.

The commercial form of industrially produced urea which is now prevalent is that of prills, i.e. small spheres having a diameter of 1-3 mm. Crystalline urea has such a great caking tendency even at very low water contents of <0.1% that it is not an option for loose storage in large amounts. An improvement in the storage properties of urea prills, which appears to be necessary, for example, in the case of silo storage of large amounts, is achieved by a subsequent surface treatment of the prills with powder substances, for example talc, bentonites, kieselguhr, diatomaceous earth or other silicatic substances, or by means of sulphur, and also by spray application of small amounts of oil. In this connection, reference is also made to conditioned urea.

Nowadays, the urea industry (Ullmann's Encyclopedia of Industrial Chemistry, Release 2006, 7th Edition) preferably adds up to 0.6% by weight of formaldehyde to the urea melt before the prilling, in order to increase the stability of the prills. This measure serves for prevention of decomposition and caking in the course of transport and for improvement of the storage stability.

The processes of EP 1 512 680, EP 1 512 681, EP 1 512 682, EP 1 593 669, EP 1 602 643, EP 1 634 868 in principle also allow the use of conditioned urea, or else any mixture of conditioned and unconditioned urea. However, preference is given to using unconditioned urea which has thus not undergone any subsequent surface treatment which serves for storage stability. The urea can be used in various administration forms (prills, granule, crystals, melt, solution).

It was a general object of the present invention to find a process for preparing cycloaliphatic diisocyanates, especially dicyclohexylmethane diisocyanate ($H_{12}MDI$), which, proceeding from the aldehyde and aromatic amine starting materials, via the intermediates of an aromatic diamine and of a cycloaliphatic diamine, works in an ecologically and economically optimized manner. At the same time, the process should as far as possible be performable without chlorine and without chlorine-containing chemicals as feedstocks and substances formed in the process, for instance hydrochloric acid or chlorides such as sodium chloride. The use of phosgene should be dispensed with. Moreover, the conversion rates (yield) of the particular feedstocks to the particular end products, taking account of the particular advantageous isomer distribution, should be high.

It was another technical object of the invention, in a first stage, to provide a process for preparing diaminodiphenylalkanes, which leads directly to the specific isomer ratio which is required for the further processing to the cycloaliphatic diamine and the corresponding diisocyanates. It is a further technical object of the invention to develop a process which works more economically viably, because it requires a shorter reaction time and leads to the desired yields of the isomers. At the same time, the formation of wastewater with a salt burden, especially of chlorine-containing salts, should be at a minimum.

The object is achieved by the present low-chlorine multistage continuous process as detailed below.

BREIF SUMMARY OF THE INVENTION

The invention provides a low-chlorine multistage and continuous process for preparing cycloaliphatic diisocyanates by
1. chlorine-free preparation of aromatic diamines (diaminodiphenylalkanes) by reacting an aromatic amine which may be substituted or unsubstituted with a $C_1$-$C_3$ aldehyde in the presence of a heterogeneous catalyst, said catalyst being a mesoporous acidic ion exchanger based on a divinylbenzene/styrene copolymer and said catalyst having acidic sites in a concentration of 2 to 6 eq/kg to DIN 54403, and the average pore diameter of the catalyst particles measured to ASTM D 4222 being 1 to 50 nm;
2. chlorine-free hydrogenation of the aromatic diamines to cycloaliphatic diamines by reacting the aromatic diamines with hydrogen in the presence of a catalyst;
3. chlorine-free or low-chlorine and continuous production of cycloaliphatic diisocyanates by reacting cycloaliphatic diamines with carbonic acid derivatives such as urea and/or urea equivalents and alcohols to give cycloaliphatic diurethanes and subsequent thermal cleavage of the diurethanes to give cycloaliphatic diisocyanates.

Advantages of the Process:

The process is performed in the 1st and 2nd stage entirely without chlorine and chlorinated chemicals and thus works in a chlorine-free manner. At the same time, during these process stages, no chlorine or chlorinated chemicals form. This achieves the effect that, firstly, no chlorinated compounds or chlorine itself get into the environment, more particularly into the air and into the wastewater. Furthermore, the plants for performing the process are protected from harmful corrosion. In the 3rd stage, phosgene is dispensed with entirely. These measures likewise protect the plants from harmful corrosion and minimize the pollution of the environment.

Particular Advantages of the Individual Stages:

1st Stage

The acidic ion exchanger used allows the hydrochloric acid normally used in the 1st stage to be dispensed with. It was additionally surprising that the acidic ion exchanger allowed the desired isomer ratio of 2,2'-, 2,4' and 4,4-diaminodiphenylalkanes to be obtained. It was likewise surprising that it was possible to substantially suppress the formation of N-methyl compounds.

2nd Stage

Advantages of the process in the hydrogenation of the aromatic diamine to the cycloaliphatic diamine are firstly an increased activity of the catalyst and an increased lifetime caused by the lack of chlorine and chlorinated chemicals in the 1st and 2nd stage of the process. Moreover, the aim pursued of achieving a trans-trans content of the hydrogenated 4,4'-diamines described in detail below was achieved.

3rd Stage

In this 3rd stage, it is very important that the reaction of the cycloaliphatic diamine to give the diisocyanate can be carried out without phosgene. The desired specific trans-trans content of the 4,4'-diisocyanate is maintained during the reaction. According to the type of catalyst which is used in the 3rd stage, this third stage is also chlorine-free when a catalyst without chlorine is used. When a catalyst containing chlorine is used, this 3rd stage works with a low chlorine content, which means that the content of chlorine (calculated as the chlorine ion, M=35.45 g/mol) is less than 100 ppm, preferably less than 50 ppm, more preferably less than 20 ppm, based on all amounts of substances present in the 3rd stage.

The process with its individual stages will be described in detail hereinafter.

DETAILED DESCRIPTION OF THE INVENTION

1st Stage

This technical problem in the first stage of the process according to the invention is solved by a process for preparing diaminodiphenylalkanes, wherein an aromatic amine which may be substituted or unsubstituted is reacted with a C1-C3 aldehyde in the presence of a heterogeneous catalyst, said catalyst being a mesoporous acidic ion exchanger based on a divinylbenzene/styrene copolymer and said catalyst having acidic sites in a concentration of 2 to 6 eq/kg to DIN 54403, and the average pore diameter of the catalyst particles measured to ASTM D 4222 being 1 to 50 nm.

Mesoporous ion exchangers are understood to mean those which possess a mean pore diameter measured to ASTM D 4222 of 1 to 50 nm. However, preference is given to using mesoporous ion exchangers with an average pore diameter of the catalyst particles measured to ASTM D 4222 of 10 to 32 nm.

In a preferred embodiment, the concentration of the acidic sites of the ion exchanger is 4.4 to 5.7 eq/kg (eq/kg means equivalents per kilogram of ion exchanger) and most preferably 4.7 to 5.6 eq/kg, measured to DIN 54 403.

The acidic sites are preferably acid groups and more preferably sulphonic acid groups.

Mesoporous ion exchangers are understood to mean those which possess a mean pore diameter, measured to ASTM D 4222, of 2 to 50 nm. According to the invention, however, mesoporous ion exchangers with an average pore diameter of the catalyst particles measured to ASTM D 4222 of 10 to 32 nm are used.

The pore diameter of the ion exchangers measured to ASTM D 4222 is preferably 15 up to and including 30 nm and most preferably 22 up to and including 30 nm.

The properties of these resins, especially specific surface area, porosity, stability and exchange capacity, can be varied by virtue of the preparation process. For example, the size of the pores and the distribution thereof can be influenced by adding porogens. Porogens are inert organic substances, for example solvents or precipitants, which are not involved in the polymerization process during the free-radical suspension polymerization. They are removed again from the polymer after the polymerization and, together with the crosslinker content, are responsible for the degree of porosity. Porogens serve as solvents for the monomers and as precipitants for the polymers formed. The porogens used in suspension polymerization are, for example, isopropanol, toluene, heptane, paraffin wax, petroleum, amyl alcohol or nitromethane.

It is possible to use acidic resins of the divinylbenzene/styrene copolymer, which are sold under the following tradenames: Duolite$^R$, Amberlyst$^R$, Amberlite$^R$, Dowex$^R$, Lewatit$^R$.

The aldehyde used is preferably formaldehyde. Formaldehyde can be used in the form of an aqueous formalin solution or else in gaseous form as formaldehyde. In addition, it is also possible to use substances which eliminate formaldehyde under the reaction conditions, for example trioxymethylene or paraformaldehyde. In a preferred manner, an aqueous formalin solution is used for the reaction.

The aromatic amines used may be substituted or unsubstituted amines. In a preferred manner, the amines should, if they are substituted, not possess any substituent in the para position. Suitable aromatic amines are, for example, N-methylaniline, N-ethylaniline, o-toluidine, o-chloroaniline, m-chloroaniline, o-anisidine, 2,3-xylidine, 3,5-xylidine, o-cyclohexylaniline, o-benzylaniline, alpha-naphthylaniline, methylmercaptoaniline or aniline. Particular preference is given to the use of aniline as the aromatic amine.

In the preparation process according to the invention, the following compositions and isomer ratios are obtained, which preferably have the following distribution:

64 to 85% by weight of 4,4'-diaminodiphenylalkane, 3 to 20% by weight, preferably 7 to 17% by weight, of 2,4'-diaminodiphenylalkane and $\leq$2% by weight of 2,2'-diaminodiphenylalkane.

The process according to the invention is preferably used to prepare diaminodiphenylmethane with the following isomer composition:

64 to 85% by weight of 4,4'-diaminodiphenylmethane, 3 to 20% by weight, preferably 7 to 17% by weight, of 2,4'-diaminodiphenylmethane and $\leq$2% by weight of 2,2'-diaminodiphenylmethane.

The proportion of polycyclic compounds in the isomer mixture of the diaminodiphenylalkane, especially of the diaminodiphenylmethane, is $\leq$15% by weight, preferably <15% by weight. In the context of the invention, polycyclic compounds are understood to mean those molecules having more than two aromatic rings, especially phenyl rings.

In the preparation process according to the invention, the following composition and isomer ratios are obtained, which more preferably have the following distribution:

74 to 85% by weight of 4,4'-diaminodiphenylalkane, 3 to 20% by weight, preferably 7 to 15% by weight, of 2,4'-diaminodiphenylalkane and $\leq$1% by weight, preferably $\leq$0.8% by weight, of 2,2'-diaminodiphenylalkane.

The process according to the invention is preferably used to prepare diaminodiphenylmethane (MDA) of the following isomer composition:

74 to 85% by weight of 4,4'-diaminodiphenylmethane, 3 to 20% by weight, preferably 7 to 15% by weight, of 2,4'-diaminodiphenylmethane and $\leq$1% by weight, preferably $\leq$0.8% by weight, of 2,2'-diaminodiphenylmethane.

In this particularly preferred variant, the proportion of polycyclic compounds in the isomer mixture of the diaminodiphenylalkane, especially of the diaminodiphenylmethane, is $\leq$10% by weight, preferably <10% by weight.

In the context of the invention, polycyclic compounds are understood to mean molecules having more than two aromatic rings, especially phenyl rings.

The N-methyl compound impurities in the isomer mixture of the diaminodiphenylalkane, especially diaminodiphenylmethane, are $\leq$1.0% by weight, preferably $\leq$0.5% by weight and more preferably $\leq$0.3% by weight. This isomer distribution is particularly suitable for being processed further via diaminodicyclohexylmethane to the corresponding diisocyanatodicyclohexylmethane compound. The isomer ratio obtained in the process according to the invention also determines the subsequent isomer ratio in the diisocyanate compound.

The process according to the invention already achieves the required isomer ratio in the diaminodiphenylalkane preparation without this isomer ratio first having to be established by additional separation processes which are inconvenient and costly. These purification processes are also disadvantageous because the substances here are very reactive substances, and so possible side reactions may also occur in the course of purification or distillation.

A further advantage of the process according to the invention is that the proportion of undesired by-products, especially N-methyl compounds, is very low. N-Methyl compounds lead, in the course of further processing to the diisocyanate, to undesired monoisocyanates and hence to a deterioration in quality of the product.

The prior art processes which work with acidic ion exchangers as catalysts lead to significantly higher isomer contents of 4,4'-diaminodiphenylalkane. For instance, the corrresponding contents in the examples of publication EP 0 043 933 are 94% by weight, 92% by weight and 91% by weight. However, these isomer contents are too high, since, in the course of further processing to the aliphatic diisocyanate compound, crystallization occurs, which is undesired.

The diaminodiphenylalkanes obtained according to EP 0 043 933 therefore have to be adjusted to the desired isomer ratio, as already described in detail above, by additional process steps such as distillation.

A further advantage of the process according to the invention lies in its ecological and economic performance. In a preferred manner, the catalytic reaction is performed at a reaction temperature in the range of 80 to 140° C., more preferably 80 to 130° C. and most preferably 80 to 120° C. The reaction time required for the catalytic reaction is preferably 30 minutes to 5 hours, more preferably 0.75 hour to 4.5 hours and most preferably 0.75 to 3.0 hours.

These reaction times are considerably lower compared to EP 0 043 933. It is evident from the examples of the publication that the reaction times here are up to 20 hours and are therefore about twenty times higher than in the process according to the invention. The reaction temperature is similarly high and this means an energy expenditure about twenty times higher in order to perform the reaction.

The process according to the invention therefore possesses the advantage that it can be performed less expensively and more economically viably and, for reasons including the shorter reaction time, offers a greater conversion per unit time.

The yields of the process according to the invention are also higher than in the prior art. For instance, the yields according to EP 0 043 933 in the examples are in the range of 60 to 78%. In comparison, overall yields of 80 to 95% are obtained in the process according to the invention.

In a preferred manner, the aromatic amine and aldehyde starting substances are used in a ratio of 5:1 to 15:1, preferably 7:1 to 12:1 and most preferably 10:1. It is preferred that the amine is used in excess, since this increases the selectivity. Excess amine can be distilled off on completion of the reaction.

The catalysts used are mesoporous acidic ion exchangers based on divinylbenzene/styrene copolymers, wherein the catalyst has acidic sites in a concentration of 2 to 6 eq/kg to DIN 54403. The catalyst can be used in the dry or moist state. The acidic groups used are preferably sulphonic acid groups. The catalyst is, for example, prepared by copolymerization of styrene with divinylbenzene and sulphonation with sulphuric acid/oleum.

The process according to the invention can preferably be performed continuously, batchwise or semicontinuously.

In a preferred version, the reaction is peformed in a stirred tank, a stirred tank cascade, a flow tube, one or more fixed bed reactors or a column. The catalytic reaction is performed over a heterogeneous catalyst.

For the performance of the process according to the invention, the aromatic amine and aldehyde starting substances are mixed continuously or batchwise. The catalytic reaction is then effected at temperatures in the range of 80 to 140° C. Subsequently, the isomer mixture of the diaminodiphenylalkanes is isolated by customary separation methods.

2nd Stage

In the 2nd stage, the invention provides a process for hydrogenating the aromatic diamines to cycloaliphatic diamines by reacting the aromatic diamines with hydrogen in the presence of a catalyst.

In principle, all aromatic diamines from the 1st stage are suitable for hydrogenation to cycloaliphatic diamines. Very particular preference is given to the hydrogenation of MDA to methylenedicyclohexyldiamine ($H_{12}$MDA).

The catalysts used may in principle be all compounds which catalyse the hydrogenation of phenyl groups. These may be homogeneous or heterogeneous catalysts; preference is given to heterogeneous catalysts.

In particular, catalysts based on nickel, cobalt, palladium, platinum, ruthenium and rhodium, alone or in a mixture, have been found to be suitable.

To increase the activity, selectivity and/or lifetime, the catalysts may additionally contain dopant metals or other modifiers. Typical dopant metals are, for example, Mo, Fe, Ag, Cr, Ni, V, Ga, In, Bi, Ti, Zr and Mn, and also the rare earths. Typical modifiers are, for example, those with which the acid-base properties of the catalysts can be influenced, for example alkali metals and alkaline earth metals or compounds thereof, and also phosphoric acid or sulphuric and compounds thereof. The catalysts may be used in the form of powders or shaped bodies, for example extrudates or pressed powders. It is possible to employ unsupported catalysts, Raney-type catalysts or supported catalysts. Suitable support materials are, for example, activated carbon, inorganic oxides, especially Al2O3, SiO2, TiO2, ZrO2, ZnO and MgO, and also bentonites, aluminosilicates, kaolins, clays and kieselguhrs, and also lithium aluminates described in documents EP 1 604 972 and EP 1 767 520. The active metal can be applied to the support material in a manner known to those skilled in the art, for example by impregnation, spray application or precipitation. According to the type of catalyst preparation, further preparation steps known to those skilled in the art are needed, for example drying, calcination, shaping and activation. For the shaping, it is optionally possible for further assistants, for example graphite or magnesium stearate, to be added.

Preference is given to using supported catalysts containing ruthenium, rhodium or Rh/Ru combinations as essential active metals. Preferred support materials are those based on Al2O3 and SiO2.

Preference is given to using those catalysts which are known to be able to prepare $H_{12}$MDA with a trans-trans content of the 4,4'-isomer between 10 and 30%, especially between 15 and 25%. Such catalysts are described, for example, in documents EP 1 366 812, EP 0 066 211, DE 100 54 347, EP 0 392 435, EP 0 630 882, EP 0 639 403 and U.S. Pat. No. 5,545,756.

Particular preference is given to hydrogenating in the presence of a supported catalyst which, as an active metal, contains ruthenium alone or together with at least one metal of transition group I, VII or VIII of the Periodic Table in an amount of 0.01 to 20% by weight of active metals, based on the supported catalyst, applied to a support.

It is known that the proportion of the trans-trans-4,4'-isomer is dependent not only on the catalyst alone but also on the reaction temperature, the conversion and the residence time in the reactor. The connections can be inferred by the person skilled in the art from the teachings of the documents already cited, and also an article by G. F. Allen (Chem. Ind. 1988, 33, p. 323-338). In order to be able to prepare $H_{12}MDA$ with a particular trans-trans content of the 4,4'-isomer in a controlled and reproducible manner, it is therefore important to accurately control the temperature, the conversion and the residence time in the reactor. Although this is also possible in principle in a batchwise reactor, preference is given to performing the hydrogenation in continuous reactors. Suitable reactors for the continuous hydrogenation are familiar to those skilled in the art and are described, for example, in the review article "Reactor types and their industrial application" in Ullmann's Encyclopedia of Industrial Chemistry, 7th online-edition 2007.

In a preferred embodiment of the invention, the continuous hydrogenation of aromatic diamines, especially MDA, is performed in fixed bed reactors. It has been found to be advantageous to perform the reaction in two or more reaction chambers connected in series. The advantage of this reaction regime is in particular that the reaction chambers can be heated or cooled independently of one another, thus giving rise to better control means of the trans-trans-4,4'-$H_{12}MDA$ content. A further advantage is that a decline in the catalyst activity can be balanced out in a more controlled manner by a temperature adjustment and, if required, partial catalyst changes are possible. The separate reaction chambers may, for example, be implemented by two or more series-connected fixed bed reactors, for example tube bundle reactors and/or shaft ovens. Another option consists in accommodating, in one reactor, spatially separate catalyst beds which can be heated or cooled by methods familiar to those skilled in the art. The fixed bed reactors can be operated in liquid phase mode, but preference is given to a trickle bed mode. The LHSV value is in the range of 0.01 to 1 h$^{-1}$ (=l of the aromatic amine to be hydrogenated per l of fixed bed catalyst and hour). The hydrogenation is effected at temperatures in the range of 50 to 200° C., preferably between 80 and 170° C. The hydrogen pressure is between 1 and 30 MPa, preferably between 5 and 15 MPa.

Preference is given to an embodiment in which the aromatic diamine, especially the MDA, is hydrogenated in a solvent. The proportion of the solvent is between 10 and 90%, preferably between 50 and 90%, based on the mass of the solution. Suitable solvents are, for example, primary, secondary and tertiary mono- or polyhydric alcohols such as methanol, ethanol, n- and i-propanol and 1-, 2-, i- and tert-butanol, ethylene glycol, ethylene glycol mono(C1-C3)alkyl ethers; linear ethers such as ethylene glycol di($C_1$-$C_3$)alkyl ethers; cyclic ethers such as tetrahydrofuran and dioxane; alkanes such as n- and isoalkanes having 4-12 carbon atoms, for example n-pentane, n-hexane and isooctane, and cyclic alkanes such as cyclohexane and decalin. While alcohols can lead to an alkylation of the amino groups, ethers do not have this disadvantage. The preferred solvent is tetrahydrofuran. Solvents may also be the hydrogenation product itself.

The hydrogenation can also be performed in the presence of ammonia or of a primary, secondary or tertiary amine, or of a polycyclic amine with a bridging nitrogen atom.

It is particularly preferred that the substance mixture to be hydrogenated which is used is crude MDA containing at least 70% by weight of 4,4'-diaminodiphenylmethane and 0.01 to 2% by weight of N-methyl compounds. It is likewise particularly preferred that the substance mixture to be hydrogenated contains 74-85% by weight of 4,4'-MDA, 3-20% by weight of 2,4'-MDA, less than 1% by weight of 2,2'-MDA and up to 1% by weight of N-methyl compounds. It is likewise particularly preferred that an H12MDA mixture with a trans-trans content of the 4,4' isomer in the range from 10 to 30%, especially from 15 to 25%, is obtained in the 2nd stage, for which, as described above, the reaction conditions and the catalyst are selected appropriately.

3rd Stage
General

In the 3rd stage of the process, the invention provides a multistage process for chlorine-free or low-chlorine and continuous production of cycloaliphatic diisocyanates by reacting cycloaliphatic diamines with carbonic acid derivatives (urea and/or urea equivalents, for example alkyl carbonates, alkyl carbamates) and alcohols to give cycloaliphatic diurethanes and subsequent thermal cleavage of the diurethanes to give cycloaliphatic diisocyanates, especially by preparing the cycloaliphatic diurethanes by one-stage, two-stage or else alternatively multistage processes, after they have been synthesized by reacting cycloaliphatic diamines with alcohol and urea and/or urea derivatives freeing them of low boilers, medium boilers and any high boilers, thermally cleaving the cycloaliphatic diurethanes thus purified to release the desired diisocyanate, continuously discharging a portion of the cleavage bottoms from the cleavage apparatus and, after workup or alternatively without additional purification, reurethanizing it with alcohol and recycling it into the process.

Variant I

The invention also provides, in the 3rd stage, a multistage process for continuously preparing cycloaliphatic diisocyanates of the formula (I)

OCN—R—NCO where R is a divalent cycloaliphatic hydrocarbon radical having 4 to 18, preferably 5 to 15, carbon atoms, with the proviso that the two isocyanate groups are bonded directly to a hydrocarbon cycle and at least 3 carbon atoms are arranged between them, are reacted by reacting cycloaliphatic diamines with urea and/or urea derivatives and alcohols to give cycloaliphatic diurethanes, and thermally cleaving the latter, wherein a) cycloaliphatic diamines of the formula (II)

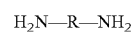

$H_2N$—R—$NH_2$ where R is a divalent cycloaliphatic hydrocarbon radical having 4 to 18, preferably 5 to 15, carbon atoms, with the proviso that the two nitrogen atoms are bonded directly to a hydrocarbon cycle and at least 3 carbon atoms are arranged between them, are reacted with urea and/or urea derivatives and alcohols of the formula (III)

$R^1$—OH where $R^1$ is a radical as remains after removal of the hydroxyl group from a primary or secondary (cyclo) aliphatic alcohol having 3 to 8 carbon atoms, in the absence or presence of dialkyl carbonates, alkyl carbamates or mixtures of dialkyl carbonates and carbamic esters, and in the absence or presence of catalysts, to give cycloaliphatic diurethanes and the ammonia formed is removed simultaneously;

b) the alcohol, the dialkyl carbonates and/or alkyl carbamates are removed from the resulting reaction mixture, and the alcohol and optionally the dialkyl carbonates and/or alkyl carbamates are recycled into reaction stage a);

c) the stream from stage b) which contains essentially diurethanes is separated by distillation into a material-of-value stream and a by-product stream which is discharged;

d) the reaction mixture which contains diurethanes and is purified via steps b) and c) is thermally cleaved continuously in the presence of a catalyst and without solvent at temperatures of 180-280° C., preferably 200-260° C., and under a pressure of 0.1-200 mbar, preferably 0.2-100 mbar, such that a portion of the reaction mixture of 10-60% by weight based on the feed, preferably 15-45% by weight based on the feed, is discharged continuously;

e) the cleavage products are separated by rectification into a crude cycloaliphatic diisocyanate and alcohol;

f) the crude cycloaliphatic diisocyanate is purified by distillation and the pure product fraction is isolated;

g) the bottoms discharge from d) is reacted with the alcohol from e) in the presence or absence of catalysts at temperatures of 20-200° C., preferably 50-170° C., and at a pressure of 0.5-20 bar, preferably 1-15 bar, over the course of 1-150 min, preferably 3-60 min, where the molar ratio of NCO groups and OH groups is up to 1:100, preferably 1:20 and more preferably 1:10;

h) a portion of the bottoms fraction from the purifying distillation f) is discharged continuously and conducted into the cleavage reaction d), but preferably the urethanization stage g);

i) the top fraction obtained in the purifying distillation of the cycloaliphatic diisocyanate is likewise recycled into the urethanization stage g) or discarded;

j) the reurethanized stream from g) is recycled into stage b), or k) the reurethanized stream from g) is recycled into the reaction stage a), with the prerequisite that g) is carried out in the presence of catalysts preferably selected from the halides of Fe(III) and/or Cu(I).

In the process according to the invention, cycloaliphatic diisocyanates can be prepared with very good selectivity without any problems in continuous operation. What is advantageous in the inventive multistage process is especially the fact that, even in the case of use of cycloaliphatic diamines of the formula (II) as the starting material for the continuous diisocyanate synthesis over a long period, a reaction which proceeds without disruption and with high selectivity is ensured.

Variant II

The invention also provides, in the 3rd stage, a multistage process for continuously preparing cycloaliphatic diisocyanates of the formula (I)

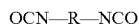

where R is a divalent cycloaliphatic hydrocarbon radical having 4 to 18, preferably 5 to 15, carbon atoms, with the proviso that the two nitrogen atoms are bonded directly to a hydrocarbon cycle and at least 3 carbon atoms are arranged between them, by reacting cycloaliphatic diamines with urea and/or urea derivatives and alcohols to give cycloaliphatic diurethanes, and thermally cleaving the latter, wherein a) cycloaliphatic diamines of the formula (II)

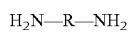

where R is a divalent cycloaliphatic hydrocarbon radical having 4 to 18, preferably 5 to 15, carbon atoms, with the proviso that the two nitrogen atoms are bonded directly to a hydrocarbon cycle and at least 3 carbon atoms are arranged between them, are reacted with urea and/or urea derivatives and alcohols of the formula (III)

where $R^1$ is a radical as remains after removal of the hydroxyl group from a primary or secondary (cyclo)aliphatic alcohol having 3 to 8 carbon atoms, in the absence or presence of dialkyl carbonates, alkyl carbamates or mixtures of dialkyl carbonates and carbamic esters, and in the absence or presence of catalysts, to give cycloaliphatic diurethanes and the ammonia formed is removed simultaneously;

b) the alcohol, the dialkyl carbonates and/or alkyl carbamates are removed from the resulting reaction mixture, and the alcohol and optionally the dialkyl carbonates and/or alkyl carbamates are recycled into reaction stage a);

c) a removal of any high-boiling residues present in the resulting reaction mixture is completely or partially dispensed with;

d) the reaction mixture which contains diurethanes and is purified via steps b) and optionally c) is thermally cleaved continuously in the presence of a catalyst and without solvent at temperatures of 180-280° C., preferably 200-260° C., and under a pressure of 0.1-200 mbar, preferably 0.2-100 mbar, such that a portion of the reaction mixture of 10-60% by weight based on the feed, preferably 15-45% by weight based on the feed, is discharged continuously;

e) the cleavage products are separated by rectification into a crude cycloaliphatic diisocyanate and alcohol;

f) the crude cycloaliphatic diisocyanate is purified by distillation and the pure product fraction is isolated;

g) the bottoms discharge from d) is reacted partially or completely with the alcohol from e) in the presence or absence of catalysts at temperatures of 20-200° C., preferably 50-170° C., and at a pressure of 0.5-20 bar, preferably 1-15 bar, over the course of 1-150 min, preferably 3-60 min, where the molar ratio of NCO groups and OH groups is up to 1:100, preferably 1:20 and more preferably 1:10;

h) the reurethanized stream from g) is separated into a material-of-value stream and a waste stream and the waste stream which is rich in high boiler components is discharged from the process and discarded;

i) a portion of the bottoms fraction of the purifying distillation f) is discharged continuously and conducted into the cleavage reaction d) or into the urethanization stage g);

j) optionally, the top fraction obtained in the purifying distillation f) of the crude cycloaliphatic diisocyanate is likewise recycled into the urethanization stage g);

k) the material-of-value stream from h) is recycled into stage a), b) or d).

In the process according to the invention, it is possible to prepare cycloaliphatic diisocyanates with very good yields without any problem in continuous operation. What is advantageous in the inventive multistage process is especially the fact that, even in the case of use of cycloaliphatic diamines of the formula (II) as the starting material for the continuous diisocyanate synthesis, deposits which are promoted especially by the high boiler components which are highly viscous by nature can be substantially prevented and good plant availability and a good process yield are also ensured in the long term. It is a further advantage of the inventive multistage process that it allows the amount of the diurethane to be converted to the vapour phase to be reduced to a minimum and in this way limits the energy demand needed.

Variant III

The invention also provides, in the 3rd stage, a multistage process for continuously preparing cycloaliphatic diisocyanates of the formula (I)

where R is a divalent cycloaliphatic hydrocarbon radical having 4 to 18, preferably 5 to 15, carbon atoms, with the proviso that the two nitrogen atoms are bonded directly to a hydrocarbon cycle and at least 3 carbon atoms are arranged between them, by reacting cycloaliphatic diamines with urea and/or urea derivatives and alcohols to give cycloaliphatic diurethanes, and thermally cleaving the latter, wherein
a) cycloaliphatic diamines of the formula (II)

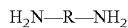

where R is a divalent cycloaliphatic hydrocarbon radical having 4 to 18, preferably 5 to 15, carbon atoms, with the proviso that the two nitrogen atoms are bonded directly to a hydrocarbon cycle and at least 3 carbon atoms are arranged between them, are reacted with urea and/or urea derivatives and alcohols of the formula (III)

where $R^1$ is a radical as remains after removal of the hydroxyl group from a primary or secondary (cyclo) aliphatic alcohol having 3 to 8 carbon atoms, in the absence or presence of dialkyl carbonates, alkyl carbamates or mixtures of dialkyl carbonates and carbamic esters, and in the absence or presence of catalysts, to give cycloaliphatic diurethanes and the ammonia formed is removed simultaneously;
b) the alcohol, the dialkyl carbonates and/or alkyl carbamates are removed from the resulting reaction mixture, and the alcohol and optionally the dialkyl carbonates and/or alkyl carbamates are recycled into reaction stage a);
c) a removal of any high-boiling residues present in the resulting reaction mixture is completely or partially dispensed with;
d) the reaction mixture which contains diurethanes and is purified via steps b) and optionally c) is thermally cleaved continuously in the presence of a catalyst and without solvent at temperatures of 180-280° C., preferably 200-260° C., and under a pressure of 0.1-200 mbar, preferably 0.2-100 mbar, such that a portion of the reaction mixture of 10-60% by weight based on the feed, preferably 15-45% by weight based on the feed, is discharged continuously;
e) the cleavage products are separated by rectification into a crude cycloaliphatic diisocyanate and alcohol;
f) the crude cycloaliphatic diisocyanate is purified by distillation and the pure product fraction is isolated;
g) the bottoms discharge from d) is separated into a material-of-value stream and a waste stream and the waste stream which is rich in high boiler components is discharged from the process and discarded;
h) the material-of-value stream from g) is reacted with the alcohol from e) in the presence or absence of catalysts at temperatures of 20-200° C., preferably 50-170° C., and at a pressure of 0.5-20 bar, preferably 1-15 bar, over the course of 1-150 min, preferably 3-60 min, where the molar ratio of NCO groups and OH groups is up to 1:100, preferably 1:20 and more preferably 1:10;
i) a portion of the bottoms fraction of the purifying distillation f) is discharged continuously and conducted into the cleavage reaction d) or into the urethanization stage h);
j) optionally, the top fraction obtained in the purifying distillation f) of the crude cycloaliphatic diisocyanate is likewise recycled into the urethanization stage h);
k) the reurethanized stream from h) is recycled into stage b); or
l) the reurethanized stream from h) is recycled into the reaction stage a), with the prerequisite that stage h) is carried out in the presence of catalysts selected from the halides of Fe(III) and/or Cu(I).

In the process according to the invention, it is possible to prepare cycloaliphatic diisocyanates with very good yields without any problem in continuous operation. What is advantageous in the inventive multistage process is especially the fact that, even in the case of use of cycloaliphatic diamines of the formula (II) as the starting material for the continuous diisocyanate synthesis, deposits which are promoted especially by the high boiler components which are highly viscous by nature can be substantially prevented and good plant availability and a good process yield are also ensured in the long term. It is a further advantage of the inventive multistage process that it allows the amount of the diurethane to be converted to the vapour phase to be reduced to a minimum and in this way limits the energy demand needed.

Variant IV

The invention also provides, in the 3rd stage, a multistage process for continuously preparing cycloaliphatic diisocyanates of the formula (I)

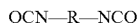

where R is a divalent cycloaliphatic hydrocarbon radical having 4 to 18, preferably 5 to 15, carbon atoms, with the proviso that the two isocyanate groups are bonded directly to a hydrocarbon cycle and at least 3 carbon atoms are arranged between them, by reacting cycloaliphatic diamines with carbonic acid derivatives and alcohols to give diurethanes, and thermally cleaving the latter, wherein
a) cycloaliphatic diamines of the formula (II)

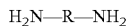

where R is a divalent cycloaliphatic hydrocarbon radical having 4 to 18, preferably 5 to 15, carbon atoms, where the two nitrogen atoms are bonded directly to at least one hydrocarbon cycle and at least 3 carbon atoms are arranged between them, are reacted with urea and in the presence of alcohols of the formula (III)

where $R^1$ is a radical as remains after removal of the hydroxyl group from a primary or secondary (cyclo) aliphatic alcohol having 3 to 8 carbon atoms, in the absence or presence of catalysts, to give cycloalkylenebisureas of the formula (IV)

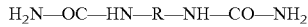

where R is a divalent cycloaliphatic hydrocarbon radical having 4 to 18, preferably 5 to 15, carbon atoms, with the proviso that the two nitrogen atoms flanking R are bonded directly to a hydrocarbon cycle and at least 3 carbon atoms are arranged between them, and the ammonia formed is simultaneously removed continuously;
b) the crude cycloalkylenebisurea obtained is converted in a second reactor using the alcohol of the formula (III) used as a solvent in a), while continuously driving out the ammonia released, to cycloalkylenediurethane of the formula (V)

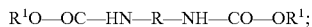

c) the alcohol, the dialkyl carbonates and/or alkyl carbamates are removed from the resulting reaction mixture and the alcohol is recycled into reaction stage a);
d) a removal of any high-boiling residues present in the resulting reaction mixture is completely or partially dispensed with;
e) the reaction mixture which contains diurethanes and is purified via steps c) and d) is thermally cleaved continuously in the presence of a catalyst and without solvent at temperatures of 180 to 280° C., preferably 200 to 260° C., and under a pressure of 0.1 to 200 mbar, preferably 0.2 to 100 mbar, such that a portion of the reaction mixture of 10 to 60% by weight based on the feed, preferably 15 to 45% by weight based on the feed, is discharged continuously;

f) the cleavage products are separated by rectification into a crude diisocyanate and alcohol;
g) the crude cycloaliphatic diisocyanate is purified by distillation and the pure product fraction is isolated;
h) the bottoms discharge from e) is separated into a material-of-value stream and a waste stream and the waste stream which is rich in high boiler components is discharged from the process and discarded;
i) the material-of-value stream from h) is reacted with the alcohol from f) in the presence or absence of catalysts at temperatures of 20 to 200° C., preferably 50 to 170° C., and at a pressure of 0.5 to 20 bar, preferably 1 to 15 bar, over the course of 1 to 150 min, preferably 3 to 60 min, where the molar ratio of NCO groups and OH groups is up to 1:100, preferably 1:20 and more preferably 1:10;
j) a portion of the bottoms fraction of the purifying distillation g) is discharged continuously and conducted into the cleavage reaction e) and/or into the urethanization stage i);
k) optionally, the top fraction obtained in the purifying distillation of the crude cycloaliphatic diisocyanate is likewise recycled into the urethanization stage i);
l) the reurethanized stream from i) is recycled into stage b) and/or c).

In the process according to the invention, it is possible to prepare cycloaliphatic diisocyanates with very good yields without any problem in continuous operation. What is advantageous in the inventive multistage process is especially the fact that, even in the case of use of cycloaliphatic diamines of the formula (II) as the starting material for the continuous diisocyanate synthesis, deposits which are promoted especially by the high boiler components which are highly viscous by nature can be substantially prevented and good plant availability and a good process yield are also ensured in the long term. It is a further advantage of the inventive multistage process that it allows the amount of the diurethane to be converted to the vapour phase to be reduced to a minimum and in this way limits the energy demand needed.

Variant V

The invention also provides, in the 3rd stage, a multistage process for continuously preparing cycloaliphatic diisocyanates of the formula (I)

OCN—R—NCO where R is a divalent cycloaliphatic hydrocarbon radical having 4 to 18, preferably 5 to 15, carbon atoms, with the proviso that the two isocyanate groups are bonded directly to a hydrocarbon cycle and at least 3 carbon atoms are arranged between them, by reacting cycloaliphatic diamines with carbonic acid derivatives and alcohols to give diurethanes, and thermally cleaving the latter, wherein
a) cycloaliphatic diamines of the formula (II)

H$_2$N—R—NH$_2$ where R is a divalent cycloaliphatic hydrocarbon radical having 4 to 18, preferably 5 to 15, carbon atoms, where the two nitrogen atoms are bonded directly to a hydrocarbon cycle and at least 3 carbon atoms are arranged between them, are reacted with urea and in the presence of alcohols of the formula (III)

R$^1$—OH where R$^1$ is a radical as remains after removal of the hydroxyl group from a primary or secondary (cyclo)aliphatic alcohol having 3 to 8 carbon atoms, in the absence or presence of catalysts, to give cycloalkylenebisureas of the formula (IV)

H$_2$N—OC—HN—R—NH—CO—NH$_2$ where R is a divalent cycloaliphatic hydrocarbon radical having 4 to 18, preferably 5 to 15, carbon atoms, with the proviso that the two nitrogen atoms flanking R are bonded directly to a hydrocarbon cycle and at least 3 carbon atoms are arranged between them, and the ammonia formed is simultaneously removed continuously;
b) the crude cycloalkylenebisurea obtained is converted in a second reactor using the alcohol of the formula (III) used as a solvent in a), while continuously driving out the ammonia released, to cycloalkylenediurethane of the formula (V)

R$^1$O—OC—HN—R—NH—CO—OR$^1$;

c) the alcohol, the dialkyl carbonates and/or alkyl carbamates are removed from the resulting reaction mixture and the alcohol is recycled into reaction stage a);
d) the stream from stage c) is separated by distillation into a material-of-value stream and a by-product stream which is discharged,
e) the reaction mixture which contains diurethanes and is purified via steps c) and d) is thermally cleaved continuously in the presence of a catalyst and without a solvent at temperatures of 180 to 280° C., preferably 200 to 260° C., and under a pressure of 0.1 to 200 mbar, preferably 0.2 to 100 mbar, such that a portion of the reaction mixture of 10 to 60% by weight based on the feed, preferably 15 to 45% by weight based on the feed, is discharged continuously;
f) the cleavage products are separated by rectification into a crude diisocyanate and alcohol;
g) the crude cycloaliphatic diisocyanate is purified by distillation and the pure product fraction is isolated;
h) the bottoms discharge from e) is reacted with the alcohol from f) in the presence or absence of catalysts at temperatures of 20 to 200° C., preferably 50 to 170° C., and at a pressure of 0.5 to 20 bar, preferably 1 to 15 bar, over the course of 1 to 150 min, preferably 3 to 60 min, where the molar ratio of NCO groups and OH groups is up to 1:100, preferably 1:20 and more preferably 1:10;
i) optionally, the reurethanization reaction h) is performed in the presence of specific catalysts selected from the halides of Fe(III) and/or Cu(I);
j) a portion of the bottoms fraction of the purifying distillation g) is discharged continuously and conducted into the cleavage reaction e) and/or into the urethanization stage h);
k) optionally, the top fraction obtained in the purifying distillation of the crude cycloaliphatic diisocyanate is likewise recycled into the urethanization stage h);
l) the reurethanized stream from h) is recycled into stage c).

In the process according to the invention, it is possible to prepare cycloaliphatic diisocyanates with very good yield without any problem in continuous operation. Omitting the recycling of the reurethanized stream of variable composition into the diurethane preparation results in two advantages for the inventive multistage process: firstly, the diurethane reactor is burdened with a lower mass flow compared to the prior art, such that a smaller design of the reactor allows cost saving potential to be exploited. Secondly, it is ensured that the diurethane synthesis can always be performed under defined stoichiometric conditions which are optimized for the purposes of the yield.

Variant VI

The invention also provides, in the 3rd stage, a multistage process for continuously preparing cycloaliphatic diisocyanates of the formula (I)

OCN—R—NCO where R is a divalent cycloaliphatic hydrocarbon radical having 4 to 18, preferably 5 to 15, carbon atoms, with the proviso that the two isocyanate groups are bonded directly to a hydrocarbon cycle and at least 3 carbon atoms are arranged between them, by reacting cycloaliphatic diamines with carbonic acid derivatives and alcohols to give diurethanes, and thermally cleaving the latter, wherein a) cycloaliphatic diamines of the formula (II)

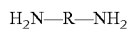

where R is a divalent cycloaliphatic hydrocarbon radical having 4 to 18, preferably 5 to 15, carbon atoms, where the two nitrogen atoms are bonded directly to at least one hydrocarbon cycle and at least 3 carbon atoms are arranged between them, are reacted with urea and in the presence of alcohols of the formula (III)

where $R^1$ is a radical as remains after removal of the hydroxyl group from a primary or secondary (cyclo) aliphatic alcohol having 3 to 8 carbon atoms, in the absence or presence of catalysts, to give cycloalkylenebisureas of the formula (IV)

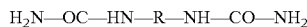

where R is a divalent cycloaliphatic hydrocarbon radical having 4 to 18, preferably 5 to 15, carbon atoms, with the proviso that the two nitrogen atoms flanking R are bonded directly to a hydrocarbon cycle and at least 3 carbon atoms are arranged between them, and the ammonia formed is simultaneously removed continuously;

b) the crude cycloalkylenebisurea obtained is converted in a second reactor using the alcohol of the formula (III) used as a solvent in a), while continuously driving out the ammonia released, to cycloalkylenediurethane of the formula (V)

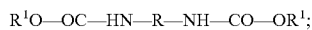

c) the alcohol, the dialkyl carbonates and/or alkyl carbamates are removed from the resulting reaction mixture and the alcohol is recycled into reaction stage a);

d) a removal of any high-boiling residues present in the resulting reaction mixture is completely or partially dispensed with;

e) the reaction mixture which contains diurethanes and is purified via steps c) and d) is thermally cleaved in the presence of a catalyst, continuously and without a solvent, at temperatures of 180 to 280° C., preferably 200 to 260° C., and under a pressure of 0.1 to 200 mbar, preferably 0.2 to 100 mbar, such that a portion of the reaction mixture of 10 to 60% by weight based on the feed, preferably 15 to 45% by weight based on the feed, is discharged continuously from the bottom;

f) the cleavage products are separated by rectification into a crude diisocyanate and alcohol;

g) the crude cycloaliphatic diisocyanate is purified by distillation and the pure product fraction is isolated;

h) the bottoms discharge from e) is reacted partially or completely with the alcohol from f) in the presence or absence of catalysts at temperatures of 20 to 200° C., preferably 50 to 170° C., and at a pressure of 0.5 to 20 bar, preferably 1 to 15 bar, over the course of 1 to 150 min, preferably 3 to 60 min, where the molar ratio of NCO groups and OH groups is up to 1:100, preferably 1:20 and more preferably 1:10;

i) the material-of-value stream from h) is separated into a material-of-value stream and a waste stream, and the waste stream which is rich in high boiler components is discharged from the process and discarded;

j) a portion of the bottoms fraction of the purifying distillation g) is discharged continuously and conducted into the cleavage reaction e) and/or into the urethanization stage h);

k) optionally, the top fraction obtained in the purifying distillation of the crude cycloaliphatic diisocyanate is likewise recycled into the urethanization stage h);

l) the purified reurethanized stream from i) is recycled into stage b) and/or c) or e).

In the process according to the invention, especially in the variants, cycloaliphatic diisocyanates can be prepared with very good yield without any problem in continuous operation. What is advantageous in the inventive multistage process is especially the fact that, even in the case of use of cycloaliphatic diamines of the formula (II) as the starting material for the continuous diisocyanate synthesis, deposits which are promoted especially by the high boiler components which are highly viscous by nature can be substantially prevented and good plant availability and good process yield are ensured even in the long term. It is a further advantage of the inventive multistage process that it allows the amount of the diurethane to be converted to the vapour phase to be reduced to a minimum and in this way limits the energy demand needed.

A further advantage is the omission of phosgene. According to the type of catalyst which is used in the 3rd stage, this 3rd stage is also chlorine-free when a catalyst without chlorine is used. When a catalyst containing chlorine is used, this 3rd stage works with a low chlorine content, which means that the content of chlorine (calculated as the chlorine ion, M=35.45 g/mol) is less than 100 ppm, preferably less than 50 ppm, more preferably less than 20 ppm, based on all amounts of substances present in the 3rd stage.

To prepare the monomeric cycloaliphatic diurethanes, the cycloaliphatic diamines of the formula (II) are reacted with urea and/or urea derivatives and an alcohol of the formula (III), possibly also mixtures of such alcohols, but possibly not preferably in the presence of dialkyl carbonates, alkyl carbamates or mixtures of dialkyl carbonates and carbamic esters, in the absence or presence of catalysts, at reaction temperatures of 100-270° C. and under a pressure of 0.5-80 bar, within 2 to 20 hours. The reaction can be effected in one stage, two stages or else more than two stages, in a continuous stirred tank cascade or in a pressure distillation reactor. The variant which proceeds via distillation reactors is preferred.

The ammonia released is driven out continuously by alcohol vapours, the amount of alcohol introduced preferably being drawn off at the top together with the ammonia formed and, after partial condensation in an alcohol recovery column, being freed from the residual ammonia and recycled into the bottom.

To increase the reaction rate, the cycloaliphatic diurethanes can be prepared in the presence of catalysts. Suitable catalysts are inorganic or organic compounds which contain one or more cations, preferably one cation, of metals of groups IA, IB, IIA, IIB, IIIA, IIIB, IVA, IVB, VA, VB, VIB, VIIB and VIIIB of the Periodic Table, defined according to Handbook of Chemistry and Physics 14th Edition, published by Chemical Rubber Publishing Co. 2310 Superior Ave. N.E. Cleveland, Ohio, for example halides such as chlorides and bromides, sulphates, phosphates, nitrates, borates, alkoxides, phenoxides, sulphonates, oxides, oxide hydrates, hydroxides, carboxylates, chelates, carbonates and thio- or dithiocarbamates. Examples include the cations of the following metals: lithium, sodium, potassium, magnesium, calcium, aluminium, gallium, tin, lead, bismuth, antimony, copper, silver, gold, zinc, mercury, cerium, titanium, vanadium, chromium, molybdenum, manganese, iron, cobalt and nickel. Examples of typical catalysts include the following compounds: lithium ethoxide, lithium butoxide, sodium methoxide, potasisum tert-butoxide, magnesium ethoxide, calcium methoxide, tin (II) chloride, tin(IV) chloride, lead acetate, aliminium trichloride, bismuth trichloride, copper(II) acetate, copper(II) chloride, zinc chloride, zinc octoate, titanium tetrabutoxide, vanadium trichloride, vanadium acetylacetonate, manganese (II) acetate, iron(II) acetate, iron(III) acetate, iron oxalate, cobalt chloride, cobalt naphthenate, nickel chloride, nickel naphthenate and mixtures thereof. The catalysts may optionally also be used in the form of their hydrates or ammoniates. It is preferred to dispense with the use of catalysts at this point. If chlorine-containing catalysts are used, the abovementioned general and preferred ranges for the chlorine content must not be exceeded.

Starting compounds for the process according to the invention are cycloaliphatic diamines of the formula (II) already mentioned above, alcohols of the formula (III) already mentioned above, and also urea and/or urea derivatives (carbonic acid derivatives) suitable as carboxylating agents, in the absence or presence of dialkyl carbonates, alkyl carbamates or mixtures of dialkyl carbonates and alkyl carbamates. The urea can be used in conditioned or unconditioned form. Preference is given to unconditioned urea, various administration forms being possible, for example prills, granule, crystals, melt, solution, suspension. Preference is given to using the urea as a melt.

In principle, all cycloaliphatic diamines of the formula (II) are suitable in accordance with the invention.

Preferred suitable diamines of the formula (II) are those such as the diamines prepared in the 2nd stage (hydrogenation), preferably 1,4-diaminocyclohexane, 4,4'-methylenedicyclohexyldiamine, 2,4-methylenedicyclohexyldiamine, 2,2'-methylenedicyclohexyldiamine ($H_{12}MDA$), i.e. perhydrogenated diaminodiphenylmethane (MDA). MDA is obtained, as described under stage 1, as an isomer mixture of 4,4'-, 2,4- and 2,2'-MDA. $H_{12}MDA$ is obtained by full hydrogenation from MDA in the 2nd stage and is accordingly a mixture of isomeric methylenedicyclohexyldiamines ($H_{12}MDA$), specifically 4,4'-, 2,4- and 2,2'-$H_{12}MDA$. Preference is given to using, as the diamines of the formula (II), 4,4'-methylenedicyclohexyldiamine, 2,4-methylenedicyclohexyldiamine and 2,2'-methylenedicyclohexyldiamine, and also any desired mixtures of at least two of these isomers.

It is particularly preferred that the diamine of the formula (II) used is an $H_{12}MDA$ mixture with at least 70% by weight of 4,4'-$H_{12}MDA$. It is likewise particularly preferred that the $H_{12}MDA$ mixture used contains 74-85% by weight of 4,4'-$H_{12}MDA$, 3-20% by weight of 2,4'-$H_{12}MDA$ and less than 1% by weight of 2,2'-$H_{12}MDA$. In addition, it is particularly preferred that an $H_{12}MDA$ mixture with a trans-trans content of the 4,4' isomer in the range from 10 to 30%, especially from 15 to 25%, is used.

Suitable alcohols of the formula (III) are any aliphatic or cycloaliphatic alcohols. Examples include C1-C6-alkanols, for example methanol, ethanol, 1-propanol, 1-butanol, 2-butanol, 1-hexanol or cyclohexanol. Preference is given to using 1-butanol as the alcohol.

In the course of the conversion of the reaction mixture, ammonia is released, the removal of which from the reaction equilibrium has been found to be advantageous. When the ammonia is discharged from the reactor, it should be ensured that the wall temperatures of the reactor and of the discharge tube are above 60° C., in order that coverage by ammonium carbamate, which is formed in minimal amounts from ammonia and carbon dioxide by decomposition of urea, can be prevented. It has, for example, been found to be useful to perform the reaction in a pressure distillation reactor. The vaporous mixture of alcohol and ammonia drawn off can, preferably under the pressure of the pressure distillation column and without condensing it beforehand, be conducted into a distillation column in order to obtain ammonia-free alcohol which is recycled into the process. In order to prevent coverage of the reflux condenser with ammonium carbamate, an appropriate proportion of alcohol to adjust the temperature at the top to at least 60° C. is permitted therein.

The excess alcohol, the dialkyl carbonates, if they have been formed or are present in the reaction mixture, or alkyl carbamates or mixtures of at least two of these components are advantageously removed in two stages. At the first stage, the reaction mixture is decompressed to a pressure of 1-500 mbar, preferably 2-150 mbar, and in this way separated into gaseous vapours which contain the predominant amount of alcohol and any dialkyl carbonates and/or alkyl carbamates, and into a liquid effluent. In the second step, the liquid effluent is freed of any residual alcohol present and also medium boilers such as dialkyl carbonates and/or alkyl carbamates by thin-film evaporation at 180-250° C., preferably 200-230° C., and a pressure of 0.1-20 mbar, preferably 1-10 mbar, such that the residue consists essentially of the monomeric polyurethane, preferably diurethane, and any high-boiling oligomers.

Subsequently, the further workup is as specified in the individual processes.

A removal of any high boilers present in the reaction mixture can optionally be dispensed with entirely or partially.

Optionally, the liquid stream from the diurethane preparation which is obtained after removal of low and medium boilers and contains monomeric diurethanes and any high-boiling oligomers can preferably be separated by distillation with the aid of a thin-film or short-path evaporator, at a temperature of 180-260° C., preferably 200-240° C., and under a pressure of 0.01-10 mbar, preferably 0.02-5 mbar, into a material-of-value stream which contains the monomeric diurethanes and the lower-boiling by-products, and an undistillable by-product stream. The undistillable by-product stream which contains the high-boiling components is discharged from the preparation process and is typically discarded as a residue which cannot be utilized as a material.

Optionally, the stream containing any high-boiling oligomers, before its above-described distillative purification, can also be divided into two substreams, of which one is fed directly to the deblocking reaction and the other initially to the above-described high boiler removal.

The material-of-value stream containing the monomeric diurethanes and the lower-boiling by-products is continuously thermally cleaved partially in a suitable apparatus, without solvent in the liquid phase, in the presence of catalysts, at temperatures of 180-280° C., preferably 200-260° C., and under a pressure of 0.1-200 mbar, preferably 0.2-100 mbar. The conversion of diurethane to diisocyanate in the apparatus for thermal cleavage can be selected substantially freely depending on the diurethane used and is typically within a range of 10-95% by weight, preferably 35-85% by weight, of the diurethane amount supplied (feed). The uncleaved fraction of the reaction mixture, which contains unconverted diurethanes, high-boiling by-products and other reutilizable and unutilizable by-products, is discharged continuously. The rate of discharge is guided by factors including the desired conversion and the desired capacity of the cleavage reaction and can easily be determined experimentally. It is typically 10-60% by weight, preferably 15-45% by weight, based on the feed.

The catalysts used for the chemical cleavage of the diurethanes are, for example, the aforementioned inorganic and organic compounds which catalyse urethane formation. Preference is given to using chlorides of zinc or of tin, and also zinc oxides, manganese oxides, iron oxides or cobalt oxides, the catalyst being metered in as a 0.01-25% by weight, preferably 0.05-10% by weight, solution or suspension, preferably in the alcohol which is also used for urethane preparation, in an amount of 5-200 ppm, preferably 10-100 ppm. The amount of chloride (calculated as the chlorine ion, M=35.45 g/mol) is less than 100 ppm, preferably less than 50 ppm, based on all amounts of substances present in the cleavage. Particular preference is given to performing the cleavage with a chlorine content, resulting from the catalyst used, of less than 20 ppm (as defined).

Suitable cleavage apparatus includes, for example, cylindrical cleavage reactors, for example tube ovens, or preferably evaporators, for example falling-film, thin-film or bulk evaporators, for example Robert evaporators, Herbert evaporators, caddie-type evaporators, Oskar evaporators and heating cartridge evaporators.

In principle, the key object is to keep the mean residence time of the isocyanate groups which are inevitably released in the course of deblocking of the alcohol in the cleavage zone to a minimum and thus to restrict undesired side reactions to a minimum.

Preference is given to performing the cleavage in a combined cleavage and rectifying column which, for the energy supply, is equipped in the bottom with a falling-film evaporator, in the lower third with a device for additional energy input or for energy recovery, in the upper third with a device for drawing off crude diisocyanate and at the top with a condenser for the reflux and the removal of pure alcohol.

The cleavage products formed in the thermal cleavage, which are composed in particular of alcohol, diisocyanate and partially cleaved diurethanes, are separated by rectification at temperatures of 95-260° C. and a pressure of 0.5-250 mbar into alcohol and into a crude diisocyanate mixture—preferably consisting of cycloaliphatic diisocyanate, partially cleaved cycloaliphatic diisocyanate and possibly small proportions of cycloaliphatic diurethanes. This separation can be carried out, for example, in the cleavage column of the above-mentioned combined cleavage and rectification column.

The crude mixture which is preferably obtained by rectification, consisting of cycloaliphatic diisocyanate, partially cleaved cycloaliphatic diurethane and possibly small proportions of cycloaliphatic diurethane, is purified by distillation at a temperature of 95-260° C. and under a pressure of 0.5-150 mbar.

The product streams discharged during the cleavage or after the cleavage or obtained by workup can be reurethanized as described above (for example variant I g) and k); variant III h) and l); variant IV i) and l)).

In this case, the appropriate reaction mixture is reacted with alcohol in the presence or absence of catalysts at temperatures of 20-200° C., preferably 50-170° C., and a pressure of 0.5-20 bar, preferably 1-15 bar, within 1-150 min, preferably 3-60 min. The reaction can be carried out in a continuous tank cascade or in a tubular reactor. Useful catalysts are in principle all catalysts which promote the NCO/OH reaction. Examples include tin octoate, dibutyltin laurate, tin dichloride, zinc dichloride and triethylamine. The reurethanization can also be carried out in the presence of Fe(III) halides or Cu(I) halides or mixtures thereof. Examples include Fe(III) chloride, Fe(III) bromide, Cu(I) chloride and Cu(I) bromide. The use of these catalysts does not rule out the simultaneous use of other catalysts which serve to accelerate the urethanization. Preference is given to using the halides of Fe(III) or Cu(I) or mixtures thereof without additional use of further catalysts. The amount of chlorine (calculated as the chlorine ion, M=35.45 g/mol) is less than 100 ppm, preferably less than 50 ppm, based on all amounts of substances present in the reaction mixture (reurethanization).

The subsequent procedure is as described in the individual processes. Further technical information regarding the individual processes can be taken by the person skilled in the art from EP 1 512 680, EP 1 512 681, EP 1 512 682, EP 1 593 669, EP 1 602 643, EP 1 634 868.

The inventive multistage process for continuously preparing cycloaliphatic diisocyanates with recycling and discharge of the by-products can be used to ensure a reaction which proceeds without disruption and with high selectivity for distillable cycloaliphatic diisocyanates over a long period. The process according to the invention is suitable especially for preparing cycloaliphatic diisocyanates having from 4 to 18, preferably 5 to 15, carbon atoms such as 1,4-diisocyanatocyclohexane, dicyclohexylmethane 4,4'-diisocyanate (4,4'-$H_{12}$MDI), dicyclohexylmethane 2,2'-diisocyanate (2,2'-$H_{12}$MDI), dicyclohexylmethane 2,4-diisocyanate (2,4-$H_{12}$MDI) or else mixtures of the aforementioned isomeric dicyclohexylmethane diisocyanates, as occur, for example, by nature in the conversion of $H_{12}$MDA (perhydrogenated MDA) in $H_{12}$MDI.

More preferably, the resulting isomer mixture of 4,4'-$H_{12}$MDI with a corresponding trans,trans content, 2,4'-$H_{12}$MDI and 2,2'-$H_{12}$MDI is prepared proceeding from the isomer mixture of 4,4'-MDA, 2,4'-MDA and 2,2'-MDA obtained with preference in the first stage, with subsequent hydrogenation to the corresponding isomer mixtures of $H_{12}$MDA.

The cycloaliphatic diisocyanates prepared are highly suitable for producing polymers containing urethane, isocyanurate, amide and/or urea groups by the polyisocyanate polyaddition process. They additionally find use for preparing polyisocyanate mixtures modified with urethane, biuret and/or isocyanurate groups. Such polyisocyanate mixtures of cycloaliphatic diisocyanates are used especially to produce high-value, light-resistant polyurethane coatings.

The process according to the invention is described below by way of example.

EXAMPLES

1st stage: Preparation of diaminodiphenylmethane (MDA)

Examples 1 and 2

232.5 g of aniline and 60 g of the moist Amberlyst 36Wet ion exchange resin containing sulphone groups were combined in a stirred vessel under an N2 atmosphere and heated to 80 or 100° C. with stirring. At these temperatures, 40 g of formaldehyde solution (37% by weight formaldehyde in water), corresponding to a molar ratio of aniline/formalin of 5:1, were metered in within 60 minutes.

The ion exchange resin used has, according to the manufacturer's product data sheet, a concentration of the acidic sites of at least 5.4 eq/kg and an average pore diameter of 240 Å (corresponds to 24 nm).

The composition of the MDA reaction product (gas chromatography analysis after subtraction of the aniline present in excess) after 60 minutes is as follows:

| No. | Temp. ° C. | 2,2'-Isomer % by wt. | 2,4'-Isomer % by wt. | 4,4'-Isomer % by wt. | N-Methyl compound % by wt. | Polycyclic compound % by wt. |
|---|---|---|---|---|---|---|
| 1 | 80 | 0.159 | 9.378 | 79.917 | 0.102 | 10.443 |
| 2 | 100 | 0.198 | 10.986 | 76.829 | 0.150 | 11.837 |

The yield is high and is 89.5% in Example 1 and 88% in Example 2.

Examples 3 to 6

232.5 g of aniline and 60 g of the moist Amberlyst 36Wet ion exchange resin containing sulphone groups were combined in a stirred vessel under an N2 atmosphere and heated to 80 or 120° C. with stirring. At these temperatures, 20 g of formaldehyde solution (37% by weight formaldehyde in water), corresponding to a molar ratio of aniline/formalin of 10:1, were metered in within 60 minutes.

The ion exchange resin used has, according to the manufacturer's product data sheet, a concentration of the acidic sites of at least 5.4 eq/kg and an average pore diameter of 240 Å (corresponds to 24 nm).

The composition of the MDA reaction product (gas chromatography analysis after subtraction of the aniline present in excess) is as follows:

| No. | Temp. ° C. | 2,2'-Isomer % by wt. | 2,4'-Isomer % by wt. | 4,4'-Isomer % by wt. | N-Methyl compound % by weight | Polycyclic compound % by wt. |
|---|---|---|---|---|---|---|
| 3 | 80 | 0.362 | 10.905 | 79.996 | 0.025 | 8.711 |
| 4 | 100 | 0.380 | 12.593 | 77.572 | 0.128 | 9.362 |
| 5 | 110 | 0.525 | 13.835 | 75.933 | 0.137 | 9.569 |
| 6 | 120 | 0.748 | 15.224 | 74.224 | 0.153 | 9.846 |

These examples too show that the required isomer ratio can be obtained without any further purification or distillation steps. The reaction times required for the full formaldehyde conversion were 240 minutes for Example 3, 140 minutes for Example 4 and 60 minutes for Examples 5 and 6. The selectivities (yields) are high and are 91.3% in Example 3, 90.5% in Example 4, 90.3% in Example 5 and 90.2% in Example 6.

Example 7

232.5 g of aniline and 60 g of the moist Amberlyst 15Wet ion exchange resin containing sulphone groups were combined in a stirred vessel under an N$_2$ atmosphere and heated to 100° C. with stirring. The ion exchange resin used has, according to the manufacturer's product data sheet, a concentration of the acidic sites of at least 4.7 eq/kg and an average pore diameter of 300 Å (corresponds to 30 nm). At this temperature, 20 g of formaldehyde solution (37% by weight formaldehyde in water), corresponding to a molar ratio of aniline/formalin of 10:1, were metered in within 60 minutes.

The composition of the reaction product (gas chromatography analysis after subtraction of the aniline present in excess) is as follows:

| No. | Temp. ° C. | 2,2'-Isomer % by wt. | 2,4'-Isomer % by wt. | 4,4'-Isomer % by wt. | N-Methyl compound % by weight | Polycyclic compound % by wt. |
|---|---|---|---|---|---|---|
| 7 | 100 | 0.14 | 12.82 | 79.32 | 0.37 | 7.28 |

The example shows that the required isomer ratio can be obtained without any further purification or distillation steps. The reaction time required for the full formaldehyde conversion was 60 minutes for Example. The selectivity (yield) is high and is 90.3%.

Example 8

93.1 g of aniline and 10 g of the moist Amberlyst 35Wet ion exchange resin containing sulphone groups were combined in a stirred vessel under an N$_2$ atmosphere and heated to 120° C. with stirring. At this temperature, 8.1 g of formaldehyde solution (37% by weight formaldehyde in water), corresponding to a molar ratio of aniline/formalin of 10:1, were metered in within 60 minutes. The ion exchange resin used has, according to the manufacturer's product data sheet, a concentration of the acidic sites of at least 5.2 eq/kg and an average pore diameter of 300 Å (corresponds to 30 nm).

The composition of the reaction product (gas chromatography analysis after subtraction of the aniline present in excess) is as follows:

0.9% 2,2 MDA; 16.8% 2,4 MDA; 70.6% 4,4 MDA; 0.06% N-methyl-MDA and 11.7% polycyclic compounds. The yield was 88.2%.

Example 9

93.1 g of aniline and 10 g of the moist Amberlyst 39Wet ion exchange resin containing sulphone groups were combined in a stirred vessel under an N$_2$ atmosphere and heated to 120° C. with stirring. At this temperature, 8.1 g of formaldehyde solution (37% by weight formaldehyde in water), corresponding to a molar ratio of aniline/formalin of 10:1, were metered in within 60 minutes. The ion exchange resin used has, according to the manufacturer's product data sheet, a concentration of the acidic sites of at least 5.0 eq/kg and an average pore diameter of 230 Å (corresponds to 23 nm).

The composition of the reaction product (gas chromatography analysis after subtraction of the aniline present in excess) is as follows:

1.5% 2,2 MDA; 17.9% 2,4 MDA; 66.8% 4,4 MDA; 0.06% N-methyl-MDA and 13.8% polycyclic compounds. The yield was 86.1%.

Example 10

93.1 g of aniline and 10 g of the moist Amberlyst 70Wet ion exchange resin containing sulphone groups were combined in a stirred vessel under an N$_2$ atmosphere and heated to 120° C. with stirring. At this temperature, 8.1 g of formaldehyde solution (37% by weight formaldehyde in water), corresponding to a molar ratio of aniline/formalin of 10:1, were metered in within 60 minutes. The ion exchange resin used has, according to the manufacturer's product data sheet, a concentration of the acidic sites of at least 2.55 eq/kg and an average pore diameter of 220 Å (corresponds to 22 nm).

The composition of the reaction product (gas chromatography analysis after subtraction of the aniline present in excess) is as follows:

1.1% 2,2 MDA; 15.9% 2,4 MDA; 69.4% 4,4 MDA; 0.03% N-methyl-MDA and 13.6% polycyclic compounds. The yield was 86.3%.

The examples show that the required isomer ratio can be obtained without any further purification or distillation steps. The selectivity (S) of the reaction is calculated from the ratio between the amount of the desired product (P) formed (here, the sum of the 2,2',2,4' and 4,4'-isomers of MDA) and the amount of the key component (K) converted (here, formaldehyde) taking account of the stoichiometric numbers (v). For batchwise operation, the following equation therefore applies:

$$S_P = \frac{n^0}{n_K^0 - n_K} \cdot \frac{|v_K|}{v_P} \cdot 100$$

After the minutes specified, the full conversion of the formaldehyde used was attained. The selectivity of the reaction is therefore identical to the yield.

2nd stage: Hydrogenation of MDA

Example 1

MDA was hydrogenated in a 2.5 l autoclave equipped with a stirrer and a basket for testing fixed bed catalysts. The basket was filled with 100 ml of a ruthenium catalyst which had been obtained according to Example 3 of EP 1366812. This catalyst was used to hydrogenate 1000 g of a solution of 12.5% by weight of MDA in THF at 120° C. and 80 bar for 6 h. The end product contained 90.5% $H_{12}$MDA with a proportion of trans-trans-4,4'-$H_{12}$MDA of 19.5%, 2% of components having a lower boiling point than $H_{12}$MDA and 7.5% of components having a higher boiling point. The MDA contained 78.6% 4,4'-MDA, 11.5% 2,4'-MDA and 0.7% 2,2'-MDA.

3rd Stage: Preparation of the Diisocyanates

Example 1

Inventive preparation of dicyclohexylmethane diisocyanate ($H_{12}$MDI) from perhydrogenated methylenediphenyldiamine ($H_{12}$MDA) and urea in the presence of n-butanol—recycling of the diurethanization product into the flash stage.

The uppermost tray of a pressure distillation reactor was charged with 255.3 g/h of $H_{12}$MDA, 149.3 g/h of urea and 545 g/h of n-butanol, and the reaction mixture was boiled with continuous removal of the ammonia released at 11-14 bar, 220° C. and a mean residence time of 8.5 h. The reactor output was, together with the stream from the reurethanization, freed of excess alcohol, low boilers and medium boilers in the flash vessel at 55 mbar with subsequent thin-film evaporation at 220° C. and 2 mbar, and sent to the high boiler removal by short-path evaporation at 0.08 mbar. The remaining 605.9 g/h of bis(4-butoxycarbonylaminocyclohexyl)methane ($H_{12}$MDU) were conducted as a melt (140° C.) into the circulation system of the falling-film evaporator of the cleavage and rectification column, and deblocking reaction was carried out at a temperature of 236° C. and a bottom pressure of 10 mbar in the presence of a steady-state tin dichloride concentration of 16 ppm. The $H_{12}$MDI and butanol cleavage gases were condensed out in two series-connected condensers at 85° C. and −25° C. The about 97% pure crude $H_{12}$MDI obtained was sent to a purifying distillation to obtain 270.33 g/h of $H_{12}$MDI with a purity of >99.5%, which corresponds to a selectivity of 85%. 177.2 g/h of butanol were obtained as a top product of the cleavage and rectification column. To maintain the constancy of mass between the cleavage and rectification column and prevent deposits and blockages of the cleavage apparatus, 147.6 g/h were discharged from the circulation system and combined with 24.0 g/h of bottoms discharge from the $H_{12}$MDI purifying distillation and the top product from the cleavage and rectification column, and reurethanized. The reurethanization product was sent to the flash vessel together with the reactor output of the diurethane preparation.

Example 2

Inventive preparation of dicyclohexylmethane diisocyanate ($H_{12}$MDI) from perhydrogenated methylenediphenyldiamine ($H_{12}$MDA) and urea in the presence of n-butanol—reurethanization in the presence of CuCl and recycling of the reurethanization product into the diurethane synthesis.

The uppermost tray of a pressure distillation reactor was charged with 255.3 g/h of $H_{12}$MDA, 149.3 g/h of urea and 545 g/h of n-butanol, and also the stream from the catalytic reurethanization, and the reaction mixture was boiled with continuous removal of the ammonia released at 11-14 bar, 220° C. and a mean residence time of 8.5 h. The reactor output was, together with the stream from the reurethanization, freed of excess alcohol, low boilers and medium boilers in the flash vessel at 55 mbar with subsequent thin-film evaporation at 220° C. and 2 mbar, and sent to the high boiler removal by short-path evaporation at 0.08 mbar. The remaining 601.1 g/h of bis(4-butoxycarbonylaminocyclohexyl)methane ($H_{12}$MDU) were conducted as a melt (140° C.) into the circulation system of the falling-film evaporator of the cleavage and rectification column, and deblocking reaction was carried out at a temperature of 236° C. and a bottom pressure of 10 mbar in the presence of a steady-state tin dichloride concentration of 16 ppm. The $H_{12}$MDI and butanol cleavage gases were condensed out in two series-connected condensers at 85° C. and −25° C. The about 97% pure crude $H_{12}$MDI obtained was sent to a purifying distillation to obtain 268.2 g/h of $H_{12}$MDI with a purity of >99.5%, which corresponds to a selectivity of 84%. 175.9 g/h of butanol were obtained as a top product of the cleavage and rectification column. To maintain the constancy of mass between the cleavage and rectification column and prevent deposits and blockages of the cleavage apparatus, 145.6 g/h were discharged from the circulation system and combined with 23.9 g/h of bottoms discharge from the $H_{12}$MDI purifying distillation and the top product from the cleavage and rectification column, and reurethanized in the presence of 100 ppm of CuCl. The reurethanization product was sent to the diurethane preparation in the presence distillation reactor.

Example 3

Inventive preparation of dicyclohexylmethane diisocyanate ($H_{12}$MDI) from perhydrogenated methylenediphenyldiamine ($H_{12}$MDA) and urea in the presence of n-butanol—recycling of the diurethanization product into the flash stage.

The uppermost tray of a pressure distillation reactor was charged with 280.8 g/h of $H_{12}$MDA, 164.0 g/h of urea and 599.6 g/h of n-butanol, and the reaction mixture was boiled with continuous removal of the ammonia released at 11-14 bar, 220° C. and a mean residence time of 8.5 h. The reactor output was, together with the stream from the reurethanization, freed of excess alcohol, low boilers and medium boilers in the flash vessel at 55 mbar with subsequent thin-film evaporation at 220° C. and 2 mbar, and the remaining 779.0 g/h of bis(4-butoxycarbonylaminocyclohexyl)methane ($H_{12}$MDU) were conducted as a melt (140° C.) into the circulation system of the falling-film evaporator of the cleavage and rectification column, and deblocking reaction was carried out at a temperature of 236° C. and a bottom pressure of 9 mbar in the presence of a steady-state tin dichloride concentration of 15 ppm. The $H_{12}$MDI and butanol cleavage gases were condensed out in two series-connected condensers at 85° C. and −25° C. The about 97% pure crude $H_{12}$MDI obtained was sent to a purifying distillation to obtain 319.52 g/h of $H_{12}$MDI with a purity of >99.5%, which corresponds to a yield of 91%. 227.5 g/h of butanol were obtained as a top product of the cleavage and rectification column. To maintain the constancy of mass between the cleavage and rectification column and prevent deposits and blockages of the cleavage apparatus, a substream was discharged continuously from the circulation system and separated by means of a short-path evaporator at 235° C. and a pressure of 0.04 mbar into a high boiler-rich waste stream and a material-of-value stream. The 181.3 g/h of material-of-value stream were combined together with 24.3 g/h of bottoms discharge from the $H_{12}$MDI purifying distillation and the top product from the cleavage and rectification column, and reurethanized. The reurethanized product was sent to the flash vessel together with the reactor effluent of the diurethane preparation.

Example 4

Inventive preparation of dicyclohexylmethane diisocyanate ($H_{12}$MDI) from perhydrogenated methylenediphenyldiamine ($H_{12}$MDA) and urea in the presence of n-butanol—reurethanization in the presence of CuCl and recycling of the reurethanized product into the diurethane synthesis.

The uppermost tray of a pressure distillation reactor was charged with 282.1 g/h of $H_{12}$MDA, 164.5 g/h of urea and 600.8 g/h of n-butanol, and also the stream from the catalytic reurethanization, and the reaction mixture was boiled with continuous removal of the ammonia released at 11-14 bar, 220° C. and a mean residence time of 8.5 h. The reactor output was, together with the stream from the reurethanization, freed of excess alcohol, low boilers and medium boilers in the flash vessel at 55 mbar with subsequent thin-film evaporation at 220° C. and 2 mbar. The remaining 778.1 g/h of bis(4-butoxycarbonylaminocyclohexyl)methane ($H_{12}$MDU) were conducted as a melt (140° C.) into the circulation system of the falling-film evaporator of the cleavage and rectification column, and deblocking reaction was carried out at a temperature of 237° C. and a bottom pressure of 9 mbar in the presence of a steady-state tin dichloride concentration of 17 ppm. The $H_{12}$MDI and butanol cleavage gases were condensed out in two series-connected condensers at 85° C. and −25° C. The about 97% pure crude $H_{12}$MDI obtained was sent to a purifying distillation to obtain 318.17 g/h of $H_{12}$MDI with a purity of >99.5%, which corresponds to a yield of 90%. 228.9 g/h of butanol were obtained as a top product of the cleavage and rectification column. To maintain the constancy of mass between the cleavage and rectification column and prevent deposits and blockages of the cleavage apparatus, a substream was discharged continuously from the circulation system and separated by means of a short-path evaporator at 235° C. and a pressure of 0.04 mbar into a high boiler-rich waste stream and a material-of-value stream. The 175.6 g/h of material-of-value stream were combined together with 24.7 g/h of bottoms discharge from the $H_{12}$MDI purifying distillation and the top product from the cleavage and rectification column, and reurethanized in the presence of 100 ppm of CuCl. The reurethanization product was sent to the diurethane preparation in the pressure distillation reactor.

Example 5

Inventive preparation of dicyclohexylmethane diisocyanate ($H_{12}$MDI) from perhydrogenated methylenediphenyldiamine and urea in the presence of n-butanol—reurethanization in the presence of CuCl and recycling of the reurethanization product into the low and medium boiler removal.

The uppermost tray of a distillation reactor was charged with 275.1 g/h of $H_{12}$MDA, 162.9 g/h of urea and 590.1 g/h of n-butanol, and the reaction mixture was boiled with continuous removal of the ammonia released at standard pressure, 135° C. and a mean residence time of 8 hours. The solution of bisurea in butanol obtained in the bottom of the distillation reactor was preheated to 190° C. by means of a heat exchanger, conducted to the uppermost tray of a pressure distillation reactor and converted further at 11 to 14 bar, 220° C. and with a mean residence time of 10.5 h. 536 g/h of n-butanol were fed into the bottom of the pressure distillation reactor and the amount of alcohol drawn off together with ammonia released at the top was selected such that it corresponded to the alcohol input in the bottom. The reactor effluent was, together with the stream from the reurethanization, freed of excess alcohol, low boilers and medium boilers in the flash vessel at 55 mbar with subsequent thin-film evaporation at 220° C. and 2 mbar, and the remaining 763.2 g/h of bis(4-butoxycarbonylaminocyclohexyl)methane ($H_{12}$MDU) were conducted as a melt (140° C.) into the circulation system of the falling-film evaporator of the cleavage and rectification column, and the deblocking reaction was carried out at a temperature of 235° C. and a bottom pressure of 9 mbar in the presence of a steady-state tin dichloride concentration of 16 ppm. The $H_{12}$MDI and butanol cleavage gases were condensed out in two series-connected condensers at 85° C. and −25° C. The about 97% pure crude $H_{12}$MDI obtained was sent to a purifying distillation to obtain 309.1 g/h of $H_{12}$MDI with a purity of >99.5%, which corresponds to a yield, based on the amine, of 90%. 226.4 g/h of butanol were obtained as the top product of the cleavage and rectification column. To maintain the constancy of mass within the cleavage and rectification column and prevent deposits and blockages of the cleavage apparatus, a substream was discharged continuously from the circulation system and divided in a ratio of 80:20, and the larger amount was separated by means of a short-path evaporator at 235° C. and a pressure of 0.05 mbar into a high boiler-rich waste stream and a material-of-value stream. The 129.45 g/h of material-of-value stream were combined with 22.7 g/h of bottoms discharge from the $H_{12}$MDI purifying distillation and the top product from the cleavage and rectification column and the unpurified substream from the discharge, and reurethanized in the presence of 100 ppm of CuCl. The reurethanization product was fed to the flash vessel together with the reactor effluent of the diurethane preparation.

Comparative Example 1

Preparation of dicyclohexylmethane diisocyanate ($H_{12}$MDI) from perhydrogenated methylenediphenyldiamine ($H_{12}$MDA) and urea in the presence of n-butanol—reurethanization and recycling of the reurethanization product into the diurethane synthesis The uppermost tray of a pressure distillation reactor was charged with 255.3 g/h of $H_{12}$MDA, 149.3 g of urea and 545 g of n-butanol, and also the stream from the reurethanization, and the reaction mixture was boiled with continuous removal of the ammonia released at 11-14 bar, 220° C. and a mean residence time of 8.5 h. The reactor output was freed of excess alcohol, low boilers and medium boilers in the flash vessel at 55 mbar with subsequent thin-film evaporation at 220° C. and 2 mbar, and sent to the high boiler removal by short-path evaporation at 0.08 mbar. The remaining 575.1 g/h of bis(4-butoxycarbonylaminocyclohexyl)methane ($H_{12}$MDU) were conducted as a melt (140° C.) into the circulation system of the falling-film evaporator of the cleavage and rectification column, and deblocking reaction was carried out at a temperature of 236° C. and a bottom pressure of 10 mbar in the presence of a steady-state tin dichloride concentration of 16 ppm. The $H_{12}$MDI and butanol cleavage gases were condensed out in two series-connected condensers at 85° C. and −25° C. The about 97% pure crude $H_{12}$MDI obtained was sent to a purifying distillation to obtain 252.9 g/h of $H_{12}$MDI with a purity of >99.5%, which corresponds to a selectivity of 79%. 163.5 g/h of butanol were obtained as a top product of the cleavage and rectification column. To maintain the constancy of mass between the cleavage and rectification column and prevent deposits and blockages of the cleavage apparatus, 139.9 g/h were discharged from the circulation system and combined with 22.6 g/h of bottoms discharge from the $H_{12}$MDI purifying distillation and the top product from the cleavage and rectification column, and reurethanized. The reurethanization product was sent to the diurethane preparation in the pressure distillation reactor.

The starting selectivity of the circulation experiment was approx. 84%. However, it decreased continuously in the course of the experiment (12 h) and at the end fell below 75%.

Comparative Example 2

Preparation of dicyclohexylmethane diisocyanate ($H_{12}$MDI) from perhydrogenated methylenediphenyldiamine ($H_{12}$MDA) and urea in the presence of n-butanol—direct recycling of the cleavage discharge into the diurethane synthesis.

The uppermost tray of a pressure distillation reactor was charged with 255.3 g/h of $H_{12}$MDA, 149.3 g/h of urea and 545 g/h of n-butanol, and also the stream from the cleavage reactor discharge and the top product of the cleavage and rectification column (butanol), and the reaction mixture was boiled with continuous removal of the ammonia released at 11-14 bar, 220° C. and a mean residence time of 8.5 h. The reactor output was freed of excess alcohol, low boilers and medium boilers in the flash vessel at 55 mbar with subsequent thin-film evaporation at 220° C. and 2 mbar, and sent to the high boiler removal by short-path evaporation at 0.08 mbar. The remaining 571.8 g/h of bis(4-butoxycarbonylaminocyclohexyl)methane ($H_{12}$MDU) were conducted as a melt (140° C.) into the circulation system of the falling-film evaporator of the cleavage and rectification column, and deblocking reaction was carried out at a temperature of 236° C. and a bottom pressure of 10 mbar in the presence of a steady-state tin dichloride concentration of 16 ppm. The $H_{12}$MDI and butanol cleavage gases were condensed out in two series-connected condensers at 85° C. and −25° C. The about 97% pure crude $H_{12}$MDI obtained was sent to a purifying distillation to obtain 249.8 g/h of $H_{12}$MDI with a purity of >99.5%, which corresponds to a selectivity of 78%. 160.6 g/h of butanol were obtained as a top product of the cleavage and rectification column. To maintain the constancy of mass between the cleavage and rectification column and prevent deposits and blockages of the cleavage apparatus, 137.5 g/h were discharged from the circulation system and sent to the diurethane preparation in the pressure distillation reactor without reurethanization. 22.8 g/h of bottoms discharge from the $H_{12}$MDI purifying distillation were recycled into the circulation system of the cleavage apparatus.

The starting selectivity of the circulation experiment was approx. 83%. However, it decreased continuously in the course of the experiment (12 h) and at the end fell below 75%.

The invention claimed is:

1. A low-chlorine multistage and continuous process for preparing at least one cycloaliphatic diisocyanate, the process comprising:
   (1) reacting in a chlorine-free environment, an aromatic amine, which may be substituted or unsubstituted, with a $C_1$-$C_3$ aldehyde in the presence of a heterogeneous catalyst, said heterogeneous catalyst being a mesoporous acidic ion exchanger comprising a divinylbenzene/styrene copolymer and said catalyst having acidic sites in a concentration of 2 to 6 eq/kg to DIN 54403, and an average pore diameter of particles of said catalyst, measured to ASTM D 4222, being 1 to 50 nm, to give at least one reacted aromatic diamine;
   (2) hydrogenating, in a chlorine-free environment, the reacted aromatic diamine with hydrogen in the presence of a hydrogenation catalyst to yield at least one cycloaliphatic diamine;
   (3) reacting the at least one cycloaliphatic diamine with at least one carbonic acid derivative and at least one alcohol to give at least one cycloaliphatic diurethane; and
   subsequently thermally cleaving the at least one diurethane to give at least one cycloaliphatic diisocyanate.

2. The process according to claim 1, wherein the $C_1$-$C_3$ aldehyde is formaldehyde.

3. The process according to claim 1, wherein the aromatic amine is aniline.

4. The process according to claim 1, wherein diaminodiphenylmethane (MDA) is prepared.

5. The process according to claim 1, wherein an isomer ratio of the reacted aromatic diamine, which is a diaminodiphenylalkane, has a distribution of:
   64 to 85% by weight of 4,4'-diaminodiphenylalkane:,
   3 to 20% by weight of 2,4'-diaminodiphenylalkane; and
   ≦2% by weight of 2,2'-diaminodiphenylalkane.

6. The process according to claim 1, wherein an isomer ratio of the reacted aromatic diamine, which is a diaminodiphenylalkane, has a distribution of:
   74 to 85% by weight of 4,4'-diaminodiphenylalkane;
   3 to 20% by weight of 2,4'-diaminodiphenylalkane; and
   ≦1.0% by weight of 2,2'-diaminodiphenylalkane.

7. The process according to claim 1, wherein the reacted aromatic diamine comprises ≦1% by weight of N-methyl compounds.

8. The process according to claim 1, wherein the reacting step (1) forms a diaminodiphenylalkane having a content of polycyclic compounds of ≦15% by weight.

9. The process according to claim 1, wherein the reaction temperature is in the range of 80 to 140° C.

10. The process according to claim 1, wherein the reaction time is 30 min to 5 hours.

11. The process according to claim 1, wherein the ratio of amine to aldehyde is 5:1 to 15:1.

12. The process according to claim 1, wherein the heterogeneous catalyst is in dry or moist form.

13. The process according to claim 1, performed continuously, batchwise, or semicontinuously.

14. The process according to claim 1, performed in a stirred tank, a stirred tank cascade, a flow tube, a fixed bed reactor, or in a column.

15. The process according to claim 1, wherein the acidic sites on the heterogeneous catalyst are sulphonic acid groups.

16. The process according to claim 1, wherein the hydrogenation catalyst is at least one selected from the group consisting of unsupported catalysts, Raney catalysts, and supported catalysts.

17. The process according to claim 1, wherein the hydrogenation catalyst comprise at least one selected from the group consisting of nickel, cobalt, palladium, platinum, ruthenium, and rhodium.

18. The process according to claim 1, wherein the hydrogenation catalyst additionally comprises at least one dopant metal and/or other modifier.

19. The process according to claim 1, wherein the hydrogenation catalyst comprises at least one supported catalyst.

20. The process according to claim 1, wherein the hydrogenation catalyst comprises at least one support material selected from the group consisting of activated carbon, inorganic oxides, bentonites, aluminosilicates, kaolins, clays, kieselguhrs, and lithium aluminates.

21. The process according to claim 1, wherein the hydrogenating is effected in the presence of a supported catalyst which, as an active metal, comprises ruthenium alone or together with at least one metal of transition group I, VII, or VIII of the Periodic Table, in an amount of 0.01 to 20% by weight of active metals, based on the supported catalyst, applied to a support.

22. The process according to claim 20, wherein the support material is at least one selected from the group consisting of $Al_2O_3$, $SiO_2$, $TiO_2$, $ZrO_2$, MgO, and ZnO.

23. The process according to claim 1, wherein the hydrogenating catalyst comprises at least one selected from the group consisting of ruthenium and rhodium.

24. The process according to claim 1, wherein the hydrogenating is performed at a temperature in the range of 20 to 200° C., and a partial hydrogen pressure in the range of 3 to 30 MPa.

25. The process according to claim 1, wherein the hydrogenating is performed in a fixed bed reactor or in a tube bundle reactor.

26. The process according to claim 1, wherein the hydrogenating is performed in two or more fixed bed reactors connected in series.

27. The process according to claim 1, wherein the hydrogenating is performed continuously.

28. The process according to claim 1, wherein the reacted aromatic diamine to be hydrogenated in the hydrogenating step is crude MDA comprising at least 74% by weight of 4,4'-diaminodiphenylmethane and 0.01 to 2% by weight of N-methyl compounds.

29. The process according to claim 1, wherein the reacted aromatic diamine to be hydrogenated in the hydrogenating step comprises 74-85% by weight of 4,4'-MDA,
3-20% by weight of 2,4'-MDA;
less than 1% by weight of 2,2'-MDA; and
up to 1% by weight of N-methyl compounds.

30. The process according to claim 1, wherein the hydrogenating is performed in the presence of a solvent.

31. The process according to claim 1, wherein methylenedicyclohexyldiamine ($H_{12}$MDA) is prepared in the hydrogenating step.

32. The process according to claim 1, wherein the at least one cycloaliphatic diurethane is prepared in the reaction of step (3) by one-stage, two-stage, or else alternatively multistage processes, and freed of low boilers, medium boilers, and any high boilers after synthesis by reaction of cycloaliphatic diamines with alcohol and urea and/or urea derivatives, the at least one cycloaliphatic diurethane thus purified is cleaved thermally to release the desired diisocyanate, and a portion of the cleavage bottoms is discharged continuously from the cleavage apparatus and, after workup or optionally without additional purification, is reurethanized with alcohol and recycled into the process.

33. The process according to claim 1, wherein $H_{12}$MDI is prepared in the reaction step (3).

34. The process according to claim 1, wherein the reaction step (3) comprises a multistage process for continuously preparing cycloaliphatic diisocyanates of formula (I)

OCN—R—NCO            (I)

wherein R is a divalent cycloaliphatic hydrocarbon radical having 4 to 18 carbon atoms, with the proviso that the two isocyanate groups are bonded directly to a cyclic hydrocarbon and at least 3 carbon atoms are arranged between them,
by reacting cycloaliphatic diamines with urea and/or urea derivatives and alcohols to give cycloaliphatic diurethanes, and thermally cleaving the cycloaliphatic diurethanes, the process comprising:
a) reacting cycloaliphatic diamines of formula (II)

$H_2N$—R—$NH_2$            (II), wherein R is a divalent cycloaliphatic hydrocarbon radical having 4 to 18 carbon atoms, with the proviso that the two nitrogen atoms are bonded directly to a hydrocarbon cycle and at least 3 carbon atoms are arranged between them,
with urea and/or urea derivatives and alcohols of formula (III)

$R^1$—OH            (III), wherein $R^1$ is a radical that remains after removal of the hydroxyl group from a primary or secondary (cyclo) aliphatic alcohol having 3 to 8 carbon atoms, in the absence or presence of dialkyl carbonates, alkyl carbamates, or mixtures of dialkyl carbonates and carbamic esters, and in the absence or presence of a catalyst, to give cycloaliphatic diurethanes in a resulting reaction mixture while simultaneously removing ammonia;
b) removing the alcohol, the dialkyl carbonates and/or alkyl carbamates from the resulting reaction mixture, and recycling the alcohol and, optionally, the dialkyl carbonates and/or alkyl carbamates into the reacting step a), to give a stream;
c) separating the stream from the removing and recycling step b), which comprises essentially diurethanes, by distillation into a material-of-value stream and a by-product stream and discharging the by-product stream;
d) continuously thermally cleaving the diurethanes comprised in the material-of-value stream of a purified reaction mixture of purified steps b) and c) above in the presence of a catalyst, and without solvent, at temperatures of 180-280° C., and under a pressure of 0.1-200 mbar, to give cleavage products, thereby continually discharging a portion of the purified reaction mixture of 10-60% by weight based on feed as bottoms discharge;
e) separating the cleavage products by rectification into a crude cycloaliphatic diisocyanate and alcohol;
f) purifying the crude cycloaliphatic diisocyanate by distillation and isolating a pure product fraction comprising distilled cycloaliphatic diisocyanate, from a bottoms fraction;
g) reacting the bottoms discharge from d) with the alcohol from e) in the presence or absence of a catalyst at temperatures of 20-200° C. and at a pressure of 0.5-20 bar, preferably 1-15 bar, over the course of 1-150 min, wherein molar ratio of NCO groups and OH groups is up to 1:100;

h) continuously discharging a portion of the bottoms fraction from the purifying by distillation f) and conducting the portion of the bottoms fraction into the cleaving d) or the reacting g);

i) recycling the top fraction obtained in the purifying step f) into the reacting step g) or discarding the top fraction; and j) recycling the reurethanized stream from the reacting step g) into the removing step b), or k) recycling the reurethanized stream from the reacting step g) into the reacting step a), with the prerequisite that the reacting g) is carried out in the presence of at least one catalyst selected from the group consisting of halides of Fe(III) and halides of Cu(I).

35. The process according to claim 1, wherein the reacting step (3) comprises a multistage process for continuously preparing cycloaliphatic diisocyanates of formula (I)

OCN—R—NCO           (I), wherein R is a divalent cycloaliphatic hydrocarbon radical having 4 to 18 carbon atoms, with the proviso that the two nitrogen atoms are bonded directly to a hydrocarbon cycle and at least 3 carbon atoms are arranged between them, by reacting cycloaliphatic diamines with urea and/or urea derivatives and alcohols to give cycloaliphatic diurethanes, and thermally cleaving the cycloaliphatic diurethanes, the process comprising:

a) reacting cycloaliphatic diamines of formula (II)

$H_2N$—R—$NH_2$           (II), wherein R is a divalent cycloaliphatic hydrocarbon radical having 4 to 18 carbon atoms, with the proviso that the two nitrogen atoms are bonded directly to a hydrocarbon cycle and at least 3 carbon atoms are arranged between them, with urea and/or urea derivatives and alcohols of formula (III)

$R^1$—OH           (III), wherein $R^1$ is a radical as remains after removal of the hydroxyl group from a primary or secondary (cyclo) aliphatic alcohol having 3 to 8 carbon atoms, in the absence or presence of dialkyl carbonates, alkyl carbamates, or mixtures of dialkyl carbonates and carbamic esters, and in the absence or presence of a catalyst, to give cycloaliphatic diurethanes in a resulting reaction mixture simultaneously removing ammonia formed;

b) removing the alcohol, the dialkyl carbonates and/or alkyl carbamates from the resulting reaction mixture, and recycling the alcohol and, optionally, the dialkyl carbonates and/or alkyl carbamates into the reacting step a);

c) completely or partially dispensing with a removal of any high-boiling residues present in the resulting reaction mixture;

d) continuously thermally cleaving the diurethanes of a purified reaction mixture comprising diurethanes and purified via the removing step b) and optionally step c), in the presence of a catalyst and without solvent at temperatures of 180-280° C. and under a pressure of 0.1-200 mbar, to give cleavage products, thereby continuously discharging a portion of the purified reaction mixture of 10-60% by weight based on feed, as bottoms discharge;

e) separating the cleavage products by rectification into a crude cycloaliphatic diisocyanate and alcohol;

f) purifying the crude cycloaliphatic diisocyanate by distillation and isolating a pure product fraction comprising cycloaliphatic diisocyanate, from a bottoms faction;

g) partially or completely reacting the bottoms discharge from the step d) with the alcohol from the step e) in the presence or absence of a catalyst at temperatures of 20-200° C. and at a pressure of 0.5-20 bar over a course of 1-150 min wherein a molar ratio of NCO groups and OH groups is up to 1:100, to give a reurethanized stream;

h) separating the reurethanized stream from the step g) into a material-of-value stream and a waste stream and discharging the waste stream, which is rich in high boiler components, from the process;

i) continuously discharging a portion of the bottoms fraction of the purifying distillation f) and conducting the portion of the bottoms fraction into the cleaving step d) or into the reacting step g);

j) optionally, recycling a top fraction obtained in the purifying by distillation step f) of the crude cycloaliphatic diisocyanate into the reacting step g); and k) recycling the material-of-value stream from the step h) into the steps a), b), or d).

36. The process according to claim 1, wherein the reacting step (3) comprises a multistage process for continuously preparing cycloaliphatic diisocyanates of formula (I)

OCN—R—NCO           (I), wherein R is a divalent cycloaliphatic hydrocarbon radical having 4 to 18 carbon atoms, with the proviso that the two nitrogen atoms are bonded directly to a hydrocarbon cycle and at least 3 carbon atoms are arranged between them, by reacting cycloaliphatic diamines with urea and/or urea derivatives and alcohols to give cycloaliphatic diurethanes, and thermally cleaving the cycloaliphatic diurethanes, the process comprising a) reacting cycloaliphatic diamines of formula (II)

$H_2N$—R—$NH_2$           (II), wherein R is a divalent cycloaliphatic hydrocarbon radical having 4 to 18 carbon atoms, with the proviso that the two nitrogen atoms are bonded directly to a hydrocarbon cycle and at least 3 carbon atoms are arranged between them, with urea and/or urea derivatives and alcohols of formula (III)

$R^1$—OH           (III), wherein $R^1$ is a radical as remains after removal of the hydroxyl group from a primary or secondary (cyclo) aliphatic alcohol having 3 to 8 carbon atoms, in the absence or presence of dialkyl carbonates, alkyl carbamates, or mixtures of dialkyl carbonates and carbamic esters, and in the absence or presence of a catalyst, to give cycloaliphatic diurethanes, while simultaneously removing ammonia formed, in a resulting reaction mixture;

b) removing the alcohol, the dialkyl carbonates and/or alkyl carbamates from the resulting reaction mixture, and recycling the alcohol and, optionally, the dialkyl carbonates and/or alkyl carbamates into the reacting a);

c) completely or partially dispensing with a removal of any high-boiling residues present in the resulting reaction mixture;

d) continuously thermally cleaving the diurethanes of a purified reaction mixture comprising diurethanes and purified via the step b) and, optionally, the step c) in the presence of a catalyst and without solvent at temperatures of 180-280° C. and under a pressure of 0.1-200 mbar to give cleavage products, thereby continuously discharging a portion of the purified reaction mixture of 10-60% by weight based on feed, as bottoms discharge;

e) separating the cleavage products by rectification into a crude cycloaliphatic diisocyanate and alcohol;

f) purifying the crude cycloaliphatic diisocyanate by distillation and isolating a pure product fraction comprising cycloaliphatic diisocyanate, from a bottoms fraction;

g) separating the bottoms discharge from the step d) into a material-of-value stream and a waste stream and discharging the waste stream, which is rich in high boiler components, from the process;

h) reacting the material-of-value stream from the step g) with the alcohol from the step e) in the presence or absence of a catalyst at temperatures of 20-200° C. and at a pressure of 0.5-20 bar over a course of 1-150 min wherein a molar ratio of NCO groups and OH groups is up to 1:100, to give a reurethanized stream;

i) continuously discharging a portion of the bottoms fraction of the purifying by the distillation step f) and conducting the portion of the bottoms fraction into the cleaving step d) or into the reacting step h);

j) optionally, recycling a top fraction obtained in the purifying distillation step f) of the crude cycloaliphatic diisocyanate into the reacting step h); and k) recycling the reurethanized stream from the step h) into the removing step b);

or l) recycling the reurethanized stream from the step h) into the reacting step a), with the prerequisite that the reacting step h) is carried out in the presence of at least one catalyst selected from the group consisting of halides of Fe(III) and halides of Cu(I).

37. The process according to claim 1, wherein the reacting step (3) comprises by a multistage process for continuously preparing cycloaliphatic diisocyanates of formula (I)

$$OCN-R-NCO \qquad (I),$$

wherein R is a divalent cycloaliphatic hydrocarbon radical having 4 to 18 carbon atoms, with the proviso that the two isocyanate groups are bonded directly to a hydrocarbon cycle and at least 3 carbon atoms are arranged between them, by reacting cycloaliphatic diamines with carbonic acid derivatives and alcohols to give diurethanes, and thermally cleaving the diurethanes, the process comprising:

a) reacting cycloaliphatic diamines of formula (II)

$$H_2N-R-NH_2 \qquad (III),$$

wherein R is a divalent cycloaliphatic hydrocarbon radical having 4 to 18 carbon atoms, where the two nitrogen atoms are bonded directly to at least one hydrocarbon cycle and at least 3 carbon atoms are arranged between them, with urea and in the presence of alcohols of formula (III)

$$R^1-OH \qquad (II),$$

wherein $R^1$ is a radical as remains after removal of the hydroxyl group from a primary or secondary (cyclo)aliphatic alcohol having 3 to 8 carbon atoms, in the absence or presence of a catalyst, to give cycloalkylenebisureas of formula (IV)

$$H_2N-OC-HN-R-NH-CO-NH_2 \qquad (IV),$$

wherein R is a divalent cycloaliphatic hydrocarbon radical having 4 to 18 carbon atoms, with the proviso that the two nitrogen atoms flanking R are bonded directly to a hydrocarbon cycle and at least 3 carbon atoms are arranged between them, and simultaneously continuously removes ammonia formed, to give crude cycloalkylene bisurea;

b) converting the crude cycloalkylenebisurea in a second reactor with the alcohol of formula (III) as a solvent in the step a), while continuously driving out ammonia released, to cycloalkylenediurethane of formula (V)

$$R^1O-OC-HN-R-NH-CO-OR^1 \qquad (V);$$

c) removing the alcohol, the dialkyl carbonates and/or alkyl carbamates from the resulting reaction mixture and recycling the alcohol into the reacting step a);

d) completely or partially dispensing with a removal of any high-boiling residues present in the resulting reaction mixture, to give a purified reaction mixture comprising diurethanes;

e) continuously thermally cleaving the diurethanes from the purified reaction mixture comprising diurethanes and purified via the step c) and the step d) in the presence of a catalyst and without solvent at temperatures of 180 to 280° C. and under a pressure of 0.1 to 200 mbar to give cleavage products, thereby continuously discharging a portion of the purified reaction mixture of 10 to 60% by weight based on feed, as bottoms discharge;

f) separating the cleavage products by rectification into a crude cycloaliphatic diisocyanate and alcohol;

g) purifying the crude cycloaliphatic diisocyanate by distillation and isolating a pure product fraction comprising cycloaliphatic diisocyanate, from a bottoms fraction;

h) separating the bottoms discharge from the step e) into a material-of-value stream and a waste stream and discharging the waste stream, which is rich in high boiler components, from the process;

i) reacting the material-of-value stream from the step h) with the alcohol from the step f) in the presence or absence of a catalyst at temperatures of 20 to 200° C. and at a pressure of 0.5 to 20 bar over a course of 1 to 150 min wherein a molar ratio of NCO groups and OH groups is up to 1:100, to give a reurethanized stream;

j) continuously discharging a portion of the bottoms fraction of the purifying by the distillation step g) and conducting the portion of the bottoms fraction into the cleaving step e) and/or into the reacting step i);

k) optionally, recycling a top fraction obtained in the purifying by the distillation step g) of the crude cycloaliphatic diisocyanate into the reacting step i); and l) recycling the reurethanized stream from the step i) into the converting step b) and/or the removing step c).

38. The process according to claim 1, wherein the reacting step (3) comprises a multistage process for continuously preparing cycloaliphatic diisocyanates of the of formula (I)

$$OCN-R-NCO \qquad (I),$$

wherein R is a divalent cycloaliphatic hydrocarbon radical having 4 to 18 carbon atoms, with the proviso that the two isocyanate groups are bonded directly to a hydrocarbon cycle and at least 3 carbon atoms are arranged between them, by reacting cycloaliphatic diamines with carbonic acid derivatives and alcohols to give diurethanes, and thermally cleaving the diurethanes, the process comprising:

a) reacting cycloaliphatic diamines of formula (II)

wherein R is a divalent cycloaliphatic hydrocarbon radical having 4 to 18 carbon atoms, where the two nitrogen atoms are bonded directly to a hydrocarbon cycle and at least 3 carbon atoms are arranged between them, with urea and in the presence of alcohols of formula (III)

wherein $R^1$ is a radical as remains after removal of the hydroxyl group from a primary or secondary (cyclo) aliphatic alcohol having 3 to 8 carbon atoms, in the absence or presence of a catalyst, to give cycloalkylenebisureas of formula (IV)

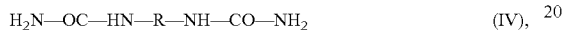

wherein R is a divalent cycloaliphatic hydrocarbon radical having 4 to 18 carbon atoms, with the proviso that the two nitrogen atoms flanking R are bonded directly to a hydrocarbon cycle and at least 3 carbon atoms are arranged between them, and simultaneously continuously removing ammonia formed, to give crude cycloalkylenebisurea;

b) converting the crude cycloalkylenebisurea obtained in a second reactor with the alcohol of formula (III) as a solvent in the step a), while continuously driving out ammonia released, to cycloalkylenediurethane of formula (V)

in a resulting reaction mixture;

c) removing the alcohol, the dialkyl carbonates and/or alkyl carbamates from the resulting reaction mixture and the recycling alcohol into the reacting step a), to give a crude stream;

d) separating the crude stream from the step c) is separated by distillation into a material-of-value stream and a by-product stream, whereby the by-product stream is discharged to give a purified reaction mixture, e) thermally cleaving the diurethanes from the purified reaction mixture comprising diurethanes and purified via the step c) and the step d) continuously in the presence of a catalyst and without a solvent at temperatures of 180 to 280° C. and under a pressure of 0.1 to 200 mbar to give cleavage products, thereby continuously discharging a portion of the reaction mixture of 10 to 60% by weight based on feed, as bottoms discharge;

separating the cleavage products by rectification into a crude cycloaliphatic diisocyanate and alcohol;

g) purifying the crude cycloaliphatic diisocyanate by distillation and isolating a pure product fraction comprising cycloaliphatic diisocyanate, from a bottoms fraction;

h) reacting the bottoms discharge from the step e) with the alcohol from the step f) in the presence or absence of a catalyst at temperatures of 20 to 200° C. and at a pressure of 0.5 to 20 bar over a course of 1 to 150 min wherein a molar ratio of NCO groups and OH groups is up to 1:100, to give a reurethanized stream;

i) optionally, performing the reacting step h) in the presence of at least one specific catalyst selected from the group consisting of halides of Fe(III) and halides of Cu(I);

j) continuously discharging a portion of the bottoms fraction of the purifying distillation step g) and conducting the portion of the bottoms fraction into the cleaving step e) and/or into the reacting step h);

k) optionally, recycling a top fraction obtained in the purifying by the distillation step g) of the crude cycloaliphatic diisocyanate into the reacting step h); and l) recycling the reurethanized stream from the step h) into the removing step c).

39. The process according to claim 1, wherein the reacting (3) comprises a multistage process for continuously preparing cycloaliphatic diisocyanates of formula (I)

wherein R is a divalent cycloaliphatic hydrocarbon radical having 4 to 18 carbon atoms, with the proviso that the two isocyanate groups are bonded directly to a hydrocarbon cycle and at least 3 carbon atoms are arranged between them, by reacting cycloaliphatic diamines with carbonic acid derivatives and alcohols to give diurethanes, and thermally cleaving the diurethanes, the process comprising:

a) recycling cycloaliphatic diamines of formula (II)

wherein R is a divalent cycloaliphatic hydrocarbon radical having 4 to 18 carbon atoms, where the two nitrogen atoms are bonded directly to at least one hydrocarbon cycle and at least 3 carbon atoms are arranged between them, with urea and in the presence of alcohols of formula (III)

wherein $R^1$ is a radical as remains after removal of the hydroxyl group from a primary or secondary (cyclo) aliphatic alcohol having 3 to 8 carbon atoms, in the absence or presence of a catalyst, to give cycloalkylenebisureas of formula (IV)

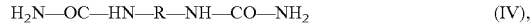

wherein R is a divalent cycloaliphatic hydrocarbon radical having 4 to 18 carbon atoms, with the proviso that the two nitrogen atoms flanking R are bonded directly to a hydrocarbon cycle and at least 3 carbon atoms are arranged between them, and simultaneously continuously removing ammonia formed, to give crude cycloalkylenebisurea;

b) converting the crude cycloalkylenebisurea obtained in a second reactor with\ the alcohol of formula (III) as a solvent in the step a), while continuously driving out ammonia released, to cycloalkylenediurethane of formula (V)

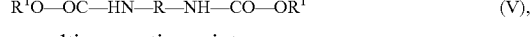

in a resulting reaction mixture;

c) removing the alcohol, the dialkyl carbonates, and/or alkyl carbamates from the resulting reaction mixture and recycling the alcohol into the reacting step a);

d) completely or partially dispensing with a removal of any high-boiling residues present in the resulting reaction mixture;

e) continuously thermally cleaving the diurethanes of a purified reaction mixture comprising diurethanes and purified via the step c) and the step d) in the presence of a catalyst, without a solvent, at temperatures of 180 to 280° C. and under a pressure of 0.1 to 200 mbar thereby continuously discharging a portion of the purified reaction mixture of 10 to 60% by weight based on feed, from the bottom as bottoms discharge;

f) separating the cleavage products by rectification into a crude cycloaliphatic diisocyanate and alcohol;

g) purifying the crude cycloaliphatic diisocyanate by distillation and isolating a pure product fraction comprising cycloaliphatic diisocyanate, from a bottoms fraction;

h) partially or completely reacting the bottoms discharge from the step e) with the alcohol from the step f) in the presence or absence of a catalyst at temperatures of 20 to 200° C. and at a pressure of 0.5 to 20 bar over a course of 1 to 150 min wherein a molar ratio of NCO groups and OH groups is up to 1:100 to give a crude stream;

i) separating the crude stream from the step h) into a material-of-value stream and a waste stream, and discharging the waste stream, which is rich in high boiler components, from the process;

j) continuously discharging a portion of the bottoms fraction of the purifying by distillation g) and conducting the portion of the bottoms fraction into the cleaving step e) and/or into the partially or completely reacting step h);

k) optionally, recycling a top fraction obtained in the purifying by the distillation step g) of the crude cycloaliphatic diisocyanate into the partially or completely reacting step h); and l) recycling the material-of-value stream from the step i) into the step b) and/or the step c) or the step e).

40. The process according to claim 1, wherein the content of chlorine, calculated as chlorine ions, M =35.45 g/mol, is less than 100 ppm based on all amounts of substances present in the reacting step (3).

41. The process according to claim 1, wherein the content of chlorine, calculated as chlorine ions, M =35.45 g/mol, is less than 100 ppm based on all amounts of substances present in the cleaving.

42. The process according to claim 1, wherein product streams discharged during the cleaving, or after the cleaving, or obtained by workup, are reurethanized, wherein the amount of chlorine, calculated as the chlorine ion, M =35.45 g/mol, is less than 100 ppm based on all amounts of substances present in a reurethanization reaction mixture.

43. The process according to claim 1, wherein conditioned urea is employed in the reacting step (3).

44. The process according to claim 43, wherein the urea is in at least one form selected from the group consisting of prills, granules, crystals, a melt, a solution, and a suspension.

45. The process according to claim 1, wherein unconditioned urea is employed in the reacting step (3).

* * * * *

UNITED STATES PATENT AND TRADEMARK OFFICE
CERTIFICATE OF CORRECTION

| | | |
|---|---|---|
| PATENT NO. | : 8,536,370 B2 | Page 1 of 1 |
| APPLICATION NO. | : 12/922280 | |
| DATED | : September 17, 2013 | |
| INVENTOR(S) | : Gerda Grund et al. | |

It is certified that error appears in the above-identified patent and that said Letters Patent is hereby corrected as shown below:

Title Page, Item (54) and in the Specification, Column 1, Line 3, the Title, "LOW CHLORINE, MULTI-STAGED METHOD FOR PRODUCING CYCLOALIPHATIC DISOCYANATES" should read "LOW CHLORINE, MULTI-STAGED METHOD FOR PRODUCING CYCLOALIPHATIC DIISOCYANATES"

Signed and Sealed this
Third Day of December, 2013

Margaret A. Focarino
*Commissioner for Patents of the United States Patent and Trademark Office*